US012303211B2

(12) United States Patent
Kemp et al.

(10) Patent No.: US 12,303,211 B2
(45) Date of Patent: *May 20, 2025

(54) SYSTEM AND METHOD FOR A TRACKED PROCEDURE

(71) Applicant: Medtronic Navigation, Inc., Louisville, CO (US)

(72) Inventors: Justin Kemp, Erie, CO (US); Yvan Paitel, Louisville, CO (US); Andrew Wald, Denver, CO (US); Trent Begin, Boulder, CO (US); Nikhil Mahendra, Broomfield, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 169 days.

This patent is subject to a terminal disclaimer.

(21) Appl. No.: 17/960,169

(22) Filed: Oct. 5, 2022

(65) Prior Publication Data

US 2023/0025480 A1    Jan. 26, 2023

Related U.S. Application Data

(63) Continuation of application No. 16/725,847, filed on Dec. 23, 2019, now Pat. No. 11,464,580, which is a
(Continued)

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/062* (2013.01); *A61B 34/10* (2016.02); *A61B 2034/2055* (2016.02); *A61B 34/30* (2016.02)

(58) Field of Classification Search
CPC ......... A61B 34/20; A61B 34/10; A61B 34/30; A61B 5/06; A61B 5/062; A61B 5/72; A61B 5/7267; G06K 9/62; G06K 9/6267
See application file for complete search history.

(56) References Cited

U.S. PATENT DOCUMENTS 7,697,972 B2    4/2010  Verard et al.
RE44,305 E      6/2013  Foley et al.
(Continued)

FOREIGN PATENT DOCUMENTS

CN    103705262 A    4/2014
EP    3443888 A1     2/2019
(Continued)

OTHER PUBLICATIONS

Glocker, et al., Automatic Localization and Identification of Vertebrae in Arbitrary Field-of-View CT Scans, 2012, 8 pgs.
(Continued)

*Primary Examiner* — Christopher J Beccia
(74) *Attorney, Agent, or Firm* — Harness, Dickey & Pierce, P.L.C.

(57) ABSTRACT

Disclosed is a navigation system. The navigation system may be used to at least assist in a procedure. The system may assist in delineating objects and/or determining physical boundaries of image elements. The system may assist in planning and/or a workflow of the procedure.

20 Claims, 9 Drawing Sheets

Related U.S. Application Data continuation of application No. 15/965,374, filed on Apr. 27, 2018, now Pat. No. 10,555,779.

(51) Int. Cl.
*A61B 34/10* (2016.01)
*A61B 34/30* (2016.01)

(56) References Cited

U.S. PATENT DOCUMENTS

| | | | |
|---|---|---|---|
| 8,644,907 | B2 | 2/2014 | Hartmann et al. |
| 8,842,893 | B2 | 9/2014 | Teichman et al. |
| 10,555,779 | B2* | 2/2020 | Kemp .................... A61B 34/20 |
| 11,464,580 | B2* | 10/2022 | Kemp .................... G16H 20/40 |
| 2004/0199072 | A1 | 10/2004 | Sprouse et al. |
| 2011/0268325 | A1* | 11/2011 | Teichman .............. A61B 34/20 382/128 |
| 2017/0112575 | A1 | 4/2017 | Li et al. |
| 2017/0193674 | A1 | 7/2017 | Haimerl |
| 2018/0061059 | A1* | 3/2018 | Xu ........................ G06T 7/174 |
| 2018/0092699 | A1 | 4/2018 | Finley |
| 2018/0250075 | A1 | 9/2018 | Cho |
| 2019/0043193 | A1 | 2/2019 | Odaibo et al. |
| 2019/0251694 | A1 | 8/2019 | Han et al. |
| 2019/0328460 | A1 | 10/2019 | Ronen et al. |

FOREIGN PATENT DOCUMENTS

| | | |
|---|---|---|
| EP | 3470006 A1 | 4/2019 |
| WO | 0056215 A1 | 9/2000 |

OTHER PUBLICATIONS

Rahman, et al., Shape-aware Deep Convolutional Neural Network for Vertebrae Segmentation, 2017, 12 pgs.
Sekuboyina, et al., A Localisation-Segmentation Approach for Multi-label Annotation of Lumbar Vertebrae using Deep Nets, 2017, 10 pgs.
Cicek, et al., 3D U-Net: Learning Dense Volumetric Segmentation from Sparse Annotation, 2016, 8 pgs.
Medtronic StealthStation® S7® System, 2013, 2 pgs.
Milletari, et al., V-Net: Fully Convolutional Neural Networks for Volumetric Medical Image Segmentation, 2016, 11 pgs.
Ioffe, et al., Batch Normalization: Accelerating Deep Network Training by Reducing Internal Covariate Shift, 2015, 11 pgs.
Dumoulin, et al., A guide to convolution arithmetic for deep learning, 2018, 31 pgs.
International Search Report and Written Opinion regarding International Application No. PCT/US2019/029147, dated Aug. 22, 2019.
Janssens Revs et al: "Fully automatic segmentation of lumbar vertebrae from CT images using cascaded 3D fully convolutional networks", 2018 IEEE 15th International Symposium On Biomedical Imaging (Isbi 2018), EEE, Apr. 4, 2018 (2018- 04-04), pp. 893-897.
Korez Robert et al: "Model-Based Segmentation of Vertebral Bodies from MR Images with 3D CNNs", Oct. 2, 2016 (Oct. 2, 2016), International Conference On Computer Analysis of Images and Patterns. CAIP 2017: Computer Analysis of Images and Patterns; [Lecture Notes in Computer Science; Lect.Notes Computer], Springer, Berlin, Heidelberg, pp. 433-441.
Md Zahangir Alom et al: "Recurrent Residual Convolutional Neural Network based on U-Net (R2U-Net) for Medical Image Segmentation", arxiv.org, Cornell University Library, 201 Olin Library Cornell University Ithaca, NY 14853, Feb. 20, 2018 (Feb. 20, 2018).
Litjens Geert et al: "A survey on deep learning in medical image analysis", Medical Image Analysis, vol. 42, Jul. 25, 2017 (Jul. 25, 2017), pp. 60-88.
International Search Report and Written Opinion regarding International Application No. PCT/US2019/029158, dated Oct. 18, 2019.
C. Cernazanu-Glavan et al, "Segmentation of Bone Structure in X-ray Images using Convolutional Neural Network", Advances in Electrical and Computer Engineering, vol. 13, No. 1, Jan. 1, 2013 (Jan. 1, 2013), p. 87-94.
Çi 525 ek Özgün et al, "3D U-Net: Learning Dense Volumetric Segmentation from Sparse Annotation", Oct. 2, 2016 (Oct. 2, 2016), International Conference On Computer Analysis of Images and Patterns. CAIP 2017: Computer Analysis of Images and Patterns; [Lecture Notes in Computer Science; Lect.Notes Computer], Springer, Berlin, Heidelberg, pp. 424-432.
Liu Wei-dong et al., A multi-step 2D/3D image registration method for minimally invasive image-guided surgery, Journal of Interventional Radiology, vol. 19, No. 11, 2010, pp. 907-910.
Zhencheng Fan et al., Spatial Position Measurement System for Surgical Navigation Using 3-D Image Marker-Based Tracking Tools With Compact Volume IEEE Transactions on Biomedical Engineering, vol. 65, No. 2, 2017, pp. 378-389.
First Chinese Office Action for related Chinese Application No. 201980028392.3; Date of Dispatch: Jan. 15, 2024; 30 pages.
European Office Action for related EP Application No. 19730231.8; Dated: May 22, 2024; 7 pages.

\* cited by examiner

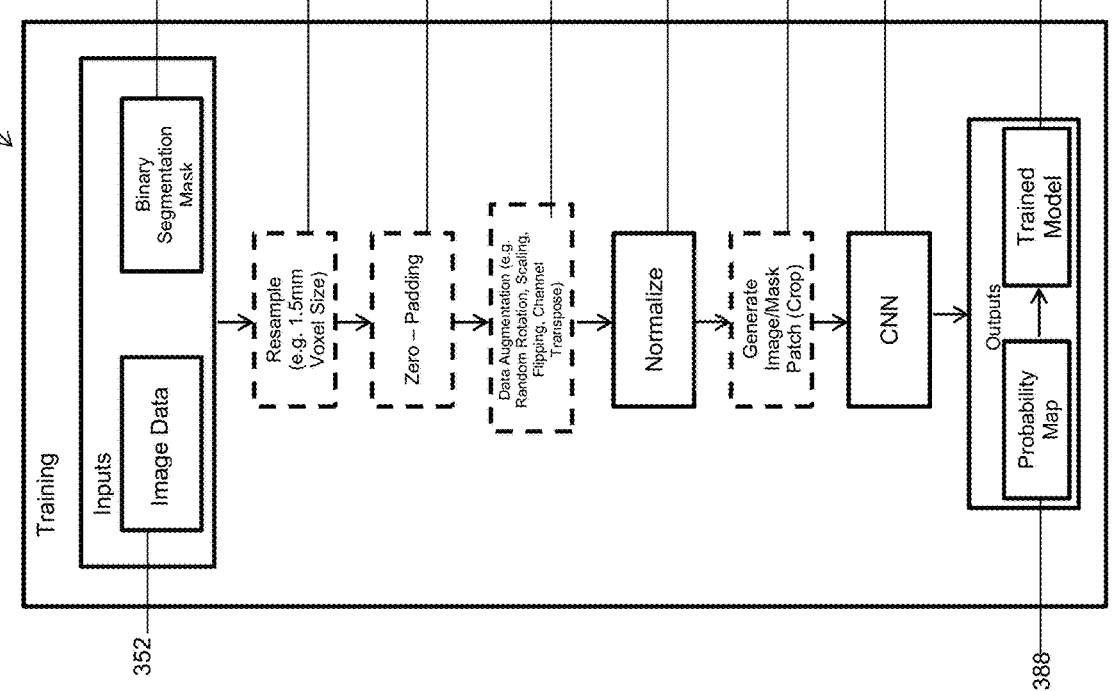

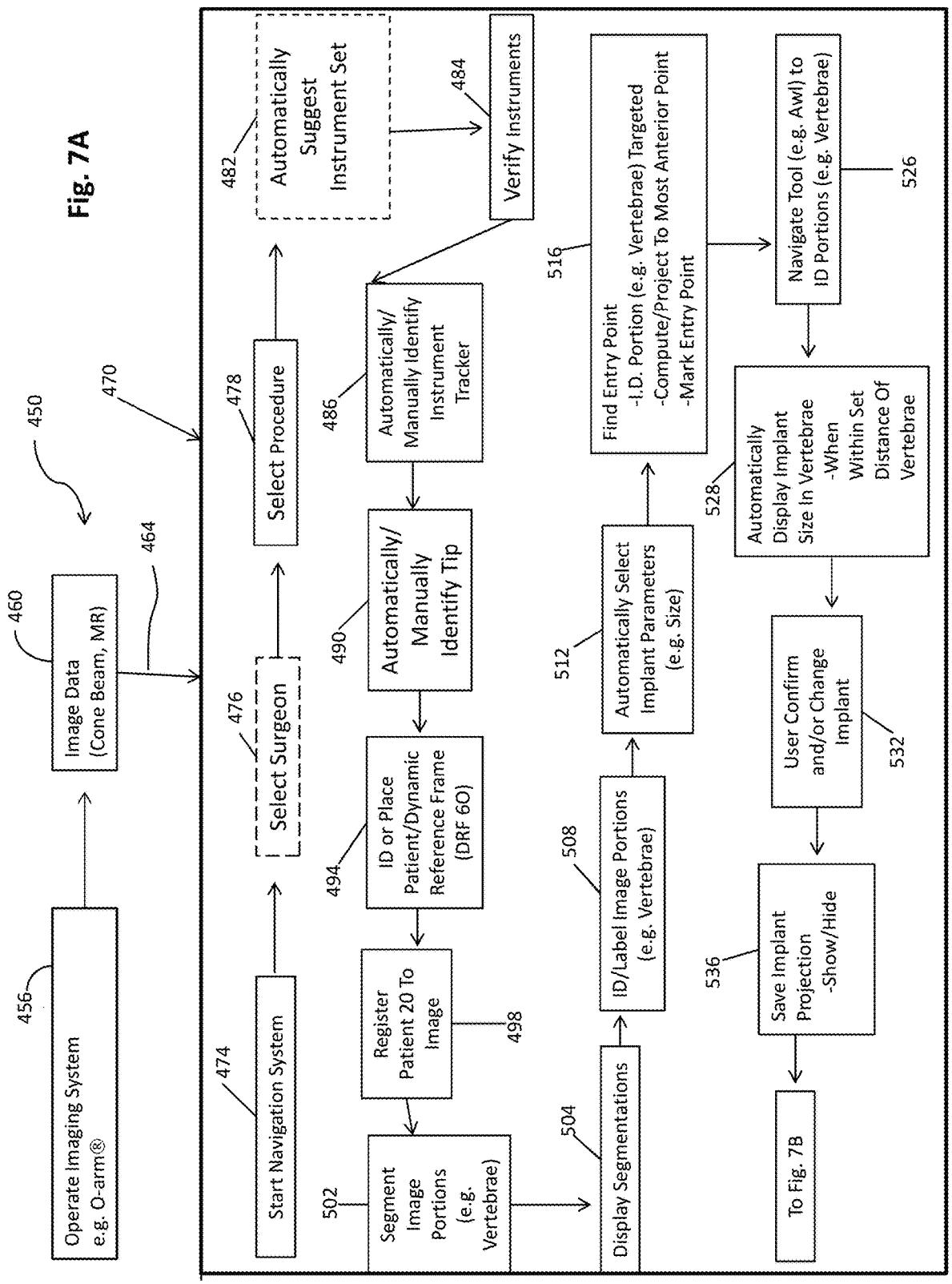

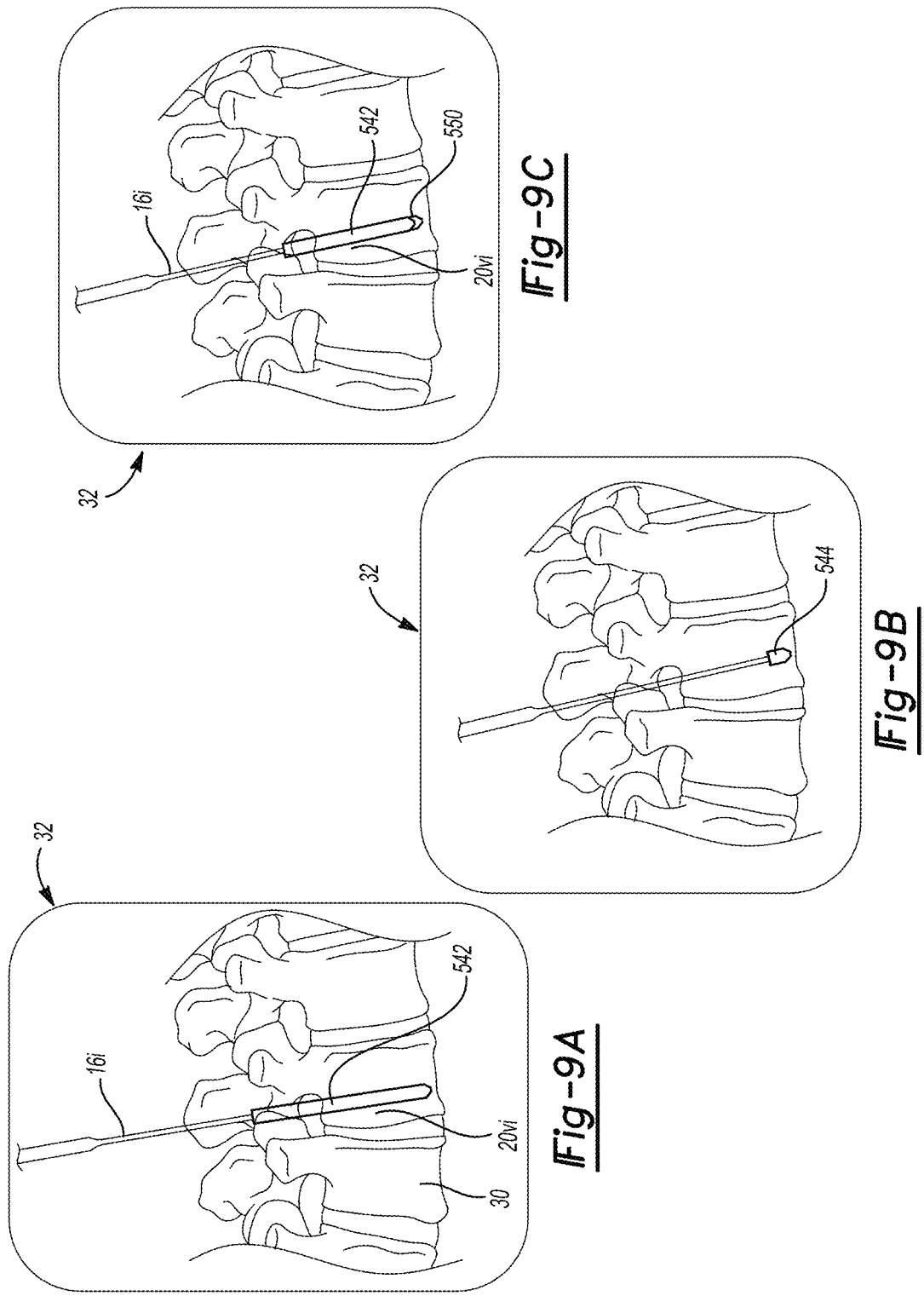

SYSTEM AND METHOD FOR A TRACKED PROCEDURE

CROSS-REFERENCE TO RELATED APPLICATIONS

This application is a continuation of U.S. application Ser. No. 16/725,847, filed Dec. 23, 2019; which is a continuation of U.S. application Ser. No. 15/965,374 filed on Apr. 27, 2018. This application also includes subject matter related to U.S. application Ser. No. 15/965,320 filed on Apr. 27, 2018. The entire disclosures of the above applications are incorporated herein by reference.

FIELD

The subject disclosure relates generally to a system and method for determining a position, including location and orientation, of a member in space relative to a subject and identifying features in an image and workflow efficiency.

BACKGROUND

This section provides background information related to the present disclosure which is not necessarily prior art.

In a navigation system for various procedures, such as surgical procedures, assembling procedures, and the like, an instrument or object may be tracked. The instrument may be tracked by one or more tracking systems of various operation modes, such as by measuring an effect of a magnetic field on a sensor coil and/or determining a location with optical sensors. The sensor coil may include a conductive material that is placed within a magnetic field where a current is induced in the sensor coil. The measured induced current may be used to identify or determine a position of the instrument or object.

The electro-magnetic field may be generated with a plurality of coils, such as three orthogonally placed coils. Various transmitter or field generation systems include the AxiEM™ electro-magnetic navigation system sold by Medtronic Navigation, Inc., having a place of business in Louisville, Colorado. The AxiEM™ electro-magnetic navigation system may include a plurality of coils that are used to generate an electro-magnetic field that is sensed by a tracking device, which may be the sensor coil, to allow a navigation system, such as a StealthStation® surgical navigation system, to be used to track and/or illustrate a tracked position of an instrument.

The tracking system may also, or alternatively, include an optical tracking system. Optical tracking systems include those such as the StealthStation® S7® tracking system. The optical tracking system includes a set of cameras with a field of vision to triangulate a position of the instrument.

SUMMARY

This section provides a general summary of the disclosure, and is not a comprehensive disclosure of its full scope or all of its features.

A system for performing a procedure is disclosed. The procedure may also be performed on a living subject such as an animal, human, or other selected patient. The procedure may include any appropriate type of procedure, such as one being performed on an inanimate object (e.g. an enclosed structure, airframe, chassis, etc.). Nevertheless, the procedure may be performed using a navigation system where a tracking system is able to track a selected one or more items.

A navigation system may be used to navigate an instrument relative to a subject for performing a procedure. In various embodiments, the procedure may include a procedure on a spine such as a spinal fusion where two or more vertebrae are connected together with a selected implant system or assembly. The implant system may include more than one component that is interconnected at a selected time. Positioning of a portion of the implant system, such as a screw, may be performed relative to a boney structure including a vertebrae. The screw may be positioned into the vertebrae along a selected trajectory and to a selected depth along the trajectory into the vertebrae. In addition to the above example, other appropriate procedures may also be performed relative to and/or on the spine or other appropriate locations.

At a selected time, such as for performing a procedure and/or planning a procedure, image data may be acquired of the subject. Image data may be used to generate an image that is displayed on the display device. The image data may include any appropriate image data such as computed tomography image data, magnetic resonance image data, X-ray cone beam image data (such as with a x-ray cone beam imager). Further, the imager may be any appropriate imager such as the O-arm® imaging system, as discussed further herein. A selected set of instructions, such as a computer vision algorithm, may be used to identify portions within the image data, such as individual vertebrae. The instructions may include a machine learning technique or process, such as a neural network system, that is programed to determine the boundaries of the vertebrae. The image data may be analyzed substantially or entirely automatically within the neural network to determine the boundaries of the vertebrae.

A selected workflow may be used to efficiently and effectively perform a procedure. The workflow may include analysis or reference to the image data to determine and/or segment selected portions or features in the image, such as segmenting specific vertebrae. The workflow may be used to operate the navigation system in an automatic manner to provide information to a user, such as a clinician or a surgeon, during the performance of the procedure. The image data, having identified boundaries of selected features (e.g. vertebra or vertebra portions), may assist or allow the system in automatically identifying a trajectory for performing a procedure, a specific implant for positioning relative to specific vertebrate, and other portions of the procedure. Accordingly, a workflow may be automated or have selected user interaction, such as reduced or faster, in performing selected and/or standard portions of a selected procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is an environmental view of a navigation system;
FIG. 2 is a schematic flowchart of a segmentation process;
FIG. 3 is a schematic view of the convolution operator
FIG. 4 is a schematic view of a CNN, according to various embodiments;

FIG. 5 is a flowchart for training a CNN, according to various embodiments;

FIG. 6 is a flowchart for a segmentation of an image with a previously trained CNN, according to various embodiments;

FIG. 7A and FIG. 7B is a flowchart for a workflow and operation of a surgical navigation system, according to various embodiments;

FIG. 9A is a display view of a proposed or planned procedure with an instrument projection;

FIG. 9B is a display view of a partially complete planned procedure with the instrument projection;

FIG. 9C is a display view of a complete planned procedure and a reverse projection.

Corresponding reference numerals indicate corresponding parts throughout the several views of the drawings.

DETAILED DESCRIPTION

Example embodiments will now be described more fully with reference to the accompanying drawings.

Figure 1:
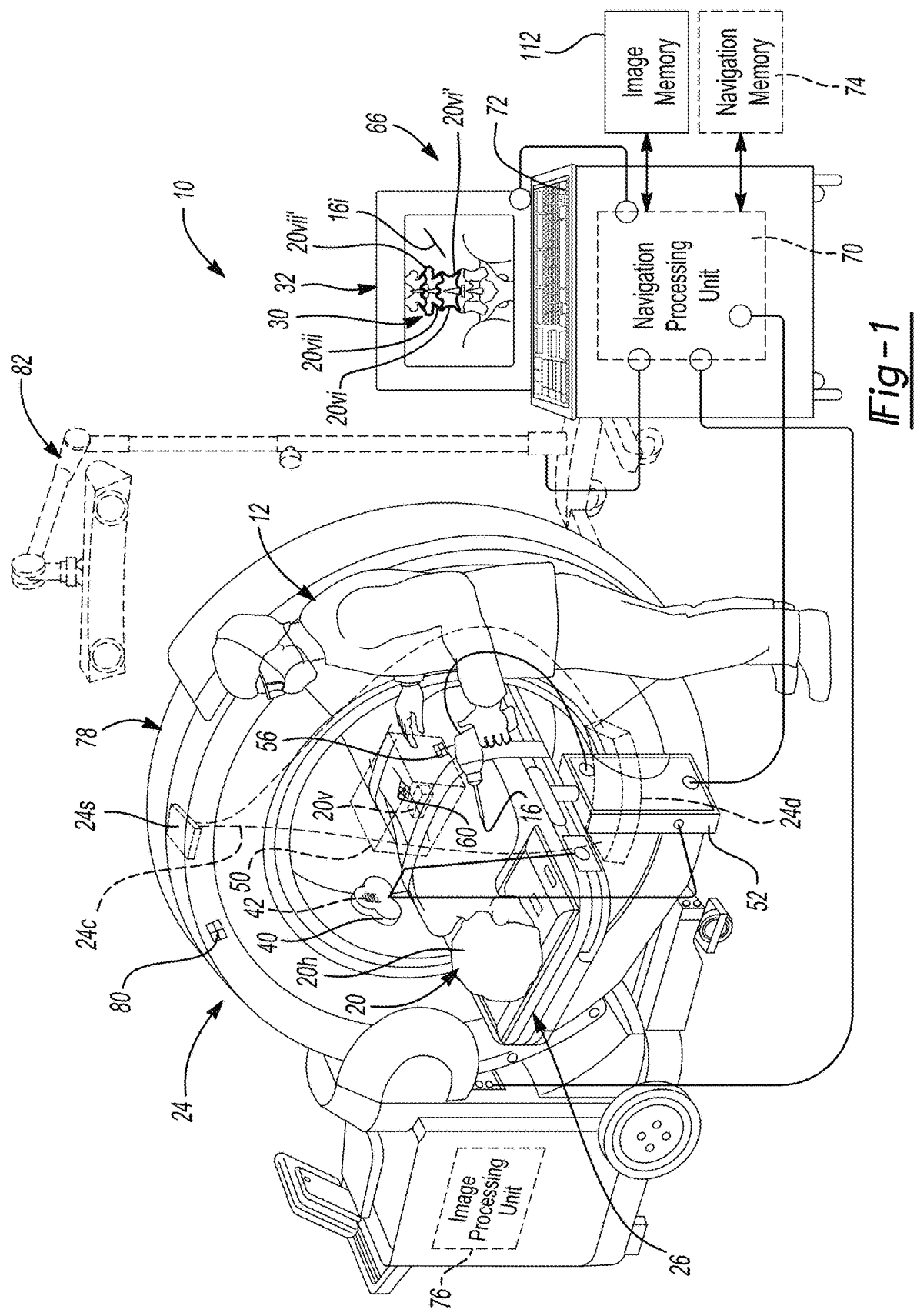

With initial reference to FIG. 1, a navigation system 10 is illustrated. The navigation system 10 may be used for various purposes or procedures by one or more users, such as a user 12. The navigation system 10 may be used to determine or track a position of an instrument 16 in a volume. The position may include both a three dimensional X,Y,Z location and orientation. Orientation may include one or more degree of freedom, such as three degrees of freedom. It is understood, however, that any appropriate degree of freedom position information, such as less than six-degree of freedom position information, may be determined and/or presented to the user 12.

Tracking the position of the instrument 16 may assist the user 12 in determining a position of the instrument 16, even if the instrument 16 is not directly viewable by the user 12. Various procedures may block the view of the user 12, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the living subject may be a human subject 20 and the procedure may be performed on the human subject 20. It is understood, however, that the instrument 16 may be tracked and/or navigated relative to any subject for any appropriate procedure. Tracking or navigating an instrument for a procedure, such as a surgical procedure, on a human or living subject is merely exemplary.

Nevertheless, in various embodiments, the surgical navigation system 10, as discussed further herein, may incorporate various portions or systems, such as those disclosed in U.S. Pat. Nos. RE44,305; 7,697,972; 8,644,907; and 8,842,893; and U.S. Pat. App. Pub. No. 2004/0199072, all incorporated herein by reference. Various components that may be used with or as a component of the surgical navigation system 10 may include an imaging system 24 that is operable to image the subject 20, such as an O-arm® imaging system, magnetic resonance imaging (MRI) system, computed tomography system, etc. A subject support 26 may be used to support or hold the subject 20 during imaging and/or during a procedure. The same or different supports may be used for different portions of a procedure.

In various embodiments, the imaging system 24 may include a source 24s. The source may emit and/or generate X-rays. The X-rays may form a cone 24c, such as in a cone beam, that impinge on the subject 20. Some of the X-rays pass though and some are attenuated by the subject 20. The imaging system 24 may further include a detector 24d to detect the X-rays that are not completely attenuated, or blocked, by the subject 20. Thus, the image data may include X-ray image data. Further, the image data may be two-dimensional (2D) image data.

Image data may be acquired, such as with one or more of the imaging systems discussed above, during a surgical procedure or acquired prior to a surgical procedure for displaying an image 30 on a display device 32. In various embodiments, the acquired image data may also be used to form or reconstruct selected types of image data, such as three-dimensional volumes, even if the image data is 2D image data. The instrument 16 may be tracked in a trackable volume or a navigational volume by one or more tracking systems. Tracking systems may include one or more tracking systems that operate in an identical manner or more and/or different manner or mode. For example, the tracking system may include an electro-magnetic (EM) localizer 40, as illustrated in FIG. 1. In various embodiments, it is understood by one skilled in the art, that other appropriate tracking systems may be used including optical, radar, ultrasonic, etc. The discussion herein of the EM localizer 40 and tracking system is merely exemplary of tracking systems operable with the navigation system 10. The position of the instrument 16 may be tracked in the tracking volume relative to the subject 20 and then illustrated as a graphical representation, also referred to as an icon, 16i with the display device 32. In various embodiments, the icon 16i may be superimposed on the image 30 and/or adjacent to the image 30. As discussed herein, the navigation system 10 may incorporate the display device 30 and operate to render the image 30 from selected image data, display the image 30, determine the position of the instrument 16, determine the position of the icon 16i, etc.

With reference to FIG. 1, the EM localizer 40 is operable to generate electro-magnetic fields with a transmitting coil array (TCA) 42 which is incorporated into the localizer 40. The TCA 42 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated will extend away from the coils 42 and form a navigation domain or volume 50, such as encompassing all or a portion of a head 20h, spinal vertebrae 20v, or other appropriate portion. The coils may be powered through a TCA controller and/or power supply 52. It is understood, however, that more than one of the EM localizers 40 may be provided and each may be placed at different and selected locations.

The navigation domain or volume 50 generally defines a navigation space or patient space. As is generally understood in the art, the instrument 16, such as a drill, lead, etc., may be tracked in the navigation space that is defined by a navigation domain relative to a patient or subject 20 with an instrument tracking device 56. For example, the instrument 16 may be freely moveable, such as by the user 12, relative to a dynamic reference frame (DRF) or patient reference frame tracker 60 that is fixed relative to the subject 20. Both the tracking devices 56, 60 may include tracking portions that are tracking with appropriate tracking systems, such as sensing coils (e.g. conductive material formed or placed in a coil) that senses and are used to measure a magnetic field strength, optical reflectors, ultrasonic emitters, etc. Due to the tracking device 56 connected or associated with the instrument 16, relative to the DRF 60, the navigation system 10 may be used to determine the position of the instrument 16 relative to the DRF 60.

The navigation volume or patient space may be registered to an image space defined by the image 30 of the subject 20 and the icon 16i representing the instrument 16 may be illustrated at a navigated (e.g. determined) and tracked position with the display device 32, such as superimposed on the image 30. Registration of the patient space to the image space and determining a position of a tracking device, such as with the tracking device 56, relative to a DRF, such as the DRF 60, may be performed as generally known in the art, including as disclosed in U.S. Pat. Nos. RE44,305; 7,697,972; 8,644,907; and 8,842,893; and U.S. Pat. App. Pub. No. 2004/0199072, all incorporated herein by reference.

The navigation system 10 may further include a navigation processor system 66. The navigation processor system 66 may include the display device 32, the TCA 40, the TCA controller 52, and other portions and/or connections thereto. For example, a wire connection may be provided between the TCA controller 52 and a navigation processing unit 70. Further, the navigation processor system 66 may have one or more user control inputs, such as a keyboard 72, and/or have additional inputs such as from communication with one or more memory systems 74, either integrated or via a communication system. The navigation processor system 66 may, according to various embodiments include those disclosed in U.S. Pat. Nos. RE44,305; 7,697,972; 8,644,907; and 8,842,893; and U.S. Pat. App. Pub. No. 2004/0199072, all incorporated herein by reference, or may also include the commercially available StealthStation® or Fusion™ surgical navigation systems sold by Medtronic Navigation, Inc. having a place of business in Louisville, CO.

Tracking information, including information regarding the magnetic fields sensed with the tracking devices 56, 60, may be delivered via a communication system, such as the TCA controller, which also may be a tracking device controller 52, to the navigation processor system 66 including the navigation processor 70. Thus, the tracked position of the instrument 16 may be illustrated as the icon 16i relative to the image 30. Various other memory and processing systems may also be provided with and/or in communication with the processor system 66, including the memory system 72 that is in communication with the navigation processor 70 and/or an imaging processing unit 76.

The image processing unit 76 may be incorporated into the imaging system 24, such as the O-arm® imaging system, as discussed above. The imaging system 24 may, therefore, include various portions such as a source and a x-ray detector that are moveable within a gantry 78. The imaging system 24 may also be tracked with a tracking device 80. It is understood, however, that the imaging system 24 need not be present while tracking the tracking devices, including the instrument tracking device 56. Also, the imaging system 24 may be any appropriate imaging system including a MRI, CT, etc.

In various embodiments, the tracking system may include an optical localizer 82. The optical localizer 82 may include one or more cameras that view or have a field of view that defines or encompasses the navigation volume 50. The optical localizer 82 may receive light (e.g. infrared or ultraviolet) input to determine a position or track the tracking device, such as the instrument tracking device 56. It is understood that the optical localizer 82 may be used in conjunction with and/or alternatively to the EM localizer 40 for tracking the instrument 16.

Information from all of the tracking devices may be communicated to the navigation processor 70 for determining a position of the tracked portions relative to each other and/or for localizing the instrument 16 relative to the image 30. The imaging system 24 may be used to acquire image data to generate or produce the image 30 of the subject 20. It is understood, however, that other appropriate imaging systems may also be used. The TCA controller 52 may be used to operate and power the EM localizer 40, as discussed above.

The image 30 that is displayed with the display device 32 may be based upon image data that is acquired of the subject 20 in various manners. For example, the imaging system 24 may be used to acquire image data that is used to generate the image 30. It is understood, however, that other appropriate imaging systems may be used to generate the image 30 using image data acquired with the selected imaging system. Imaging systems may include magnetic resonance imagers, computed tomography imagers, and other appropriate imaging systems. Further the image data acquired may be two dimensional or three dimensional data and may have a time varying component, such as imaging the patient during a heart rhythm and/or breathing cycle.

In various embodiments, the image data is a 2D image data that is generated with a cone beam. The cone beam that is used to generate the 2D image data may be part of an imaging system, such as the O-arm® imaging system. The 2D image data may then be used to reconstruct a 3D image or model of the imaged subject, such as the patient 20. The reconstructed 3D image and/or an image based on the 2D image data may be displayed. Thus, it is understood by one skilled in the art that the image 30 may be generated using the selected image data.

Further, the icon 16i, determined as a tracked position of the instrument 16, may be displayed on the display device 32 relative to the image 30. In addition, the image 30 may be segmented, for various purposes, including those discussed further herein. Segmentation of the image 30 may be used determine and/or delineate objects or portions in the image. The delineation may include or be made as a mask that is represented on a display. The representation may be shown on the display such as with a graphical overlay of a mask, which may also be referred to as an icon. The icon may the segmented mask and may not be simplified in any manner. In various embodiments, the delineation may be used to identify boundaries of various portions within the image 30, such as boundaries of one or more structures of the patient that is imaged, such as the vertebrae 20v. Accordingly, the image 30 may include an image of one or more of the vertebrae 20v, such as a first vertebrae 20vi and a second vertebrae 20vii. As discussed further herein, the vertebrae, such as the first and second vertebrae 20vi, 20vii may be delineated in the image which may include and/or assist in determining boundaries in images, such as 3D and 2D images. In various embodiments, the delineation may be represented such as with an icon 20vi' or a second icon 20vii'. The boundaries 20vi', 20vii' may be determined in an appropriate manner and for various purposes, as also discussed further herein. Further, the icon may be used to represent, for display, a selected item, as discussed herein, including the delineation of the object, boundary, etc.

According to various embodiments, the image 30 may be segmented in a substantially automatic manner. In various embodiments, the automatic segmentation may be incorporated into a neural network, such as a convolutional neural network (CNN). The CNN may be taught or learn to determine, such as with a probability or prediction, various features, according to various embodiments. Various features may include objects (e.g. vertebra) or parts or portions of objects (e.g. pedicle), and segmentations or boundaries of these objects or portions. The selected segmentations may include identifying a segmentation of selected vertebrae, such as the first vertebrae 20vi and the second vertebrae 20vii. The selected segmentation may be displayed with a selected graphical representation such as a segmentation icon or representation 20vi' and 20vii' for display on the display device 32.

The icons are displayed alone on the display 32 and/or superimposed on the image 30 for viewing by a selected user, such as the user 12 which may be a surgeon or other appropriate clinician. Moreover, once identified, the boundaries or other appropriate portion, whether displayed as icons or not, may be used for various purposes. The boundaries may identify a physical dimension of the vertebrae, positions of the vertebrae in space (i.e. due to registration of the image 30 to the subject 20 as discussed above), possible identified trajectories (e.g. for implantation placement), or the like. Therefore, the image 30 may be used in planning and/or performing a procedure whether the icons 20vi', 20vii' are displayed or the geometry of the boundaries is only determined and not displayed as an icon.

Figure 2:
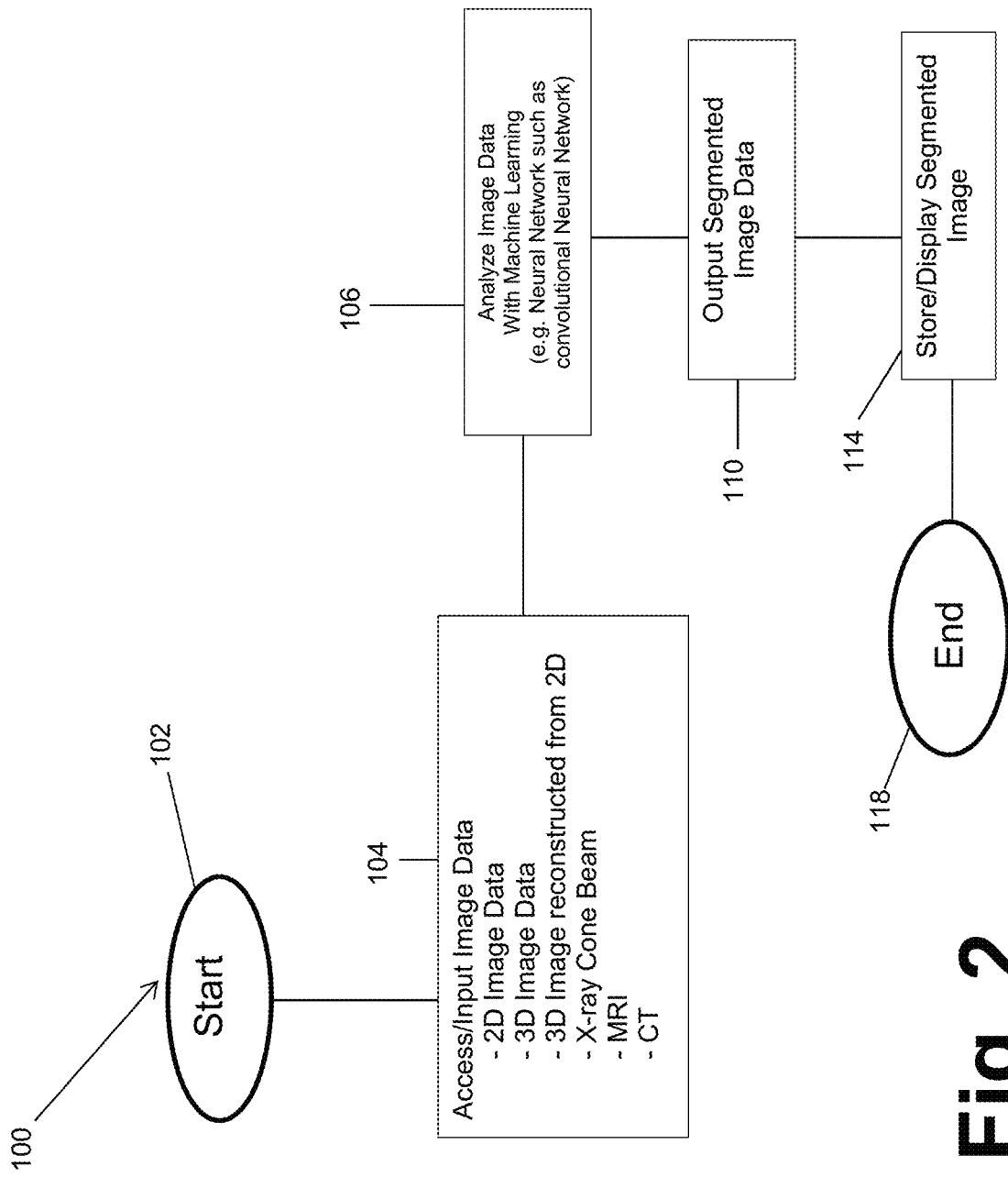

Turning reference to FIG. 2, a process or method for identifying a portion of an image, also referred to as segmenting an image, is illustrated in the flowchart 100. The flowchart 100, is a general flowchart and a more specific process, such as a CNN, will be discussed in further detail herein. Generally, however, the segmentation process begins with an input of image data. The image data may include any appropriate image data such as computed tomography image data, magnetic resonance image data, X-ray cone beam image data. Further, the imager may be any appropriate imager such as the O-arm® imaging system, as discussed herein. The O-arm® imaging system may be configured to acquire image data for a 360 degrees around a subject and include 2D image data and/or a 3D reconstruction based on the 2D image data. Further, the O-arm® imaging system may generate images with a x-ray cone beam.

The image data may include 2D image data or a 3D model reconstructed from the 2D image data in block 104. The 2D image data or the reconstructed 3D image data may be from an imaging system such as the imaging system 24. The imaging system 24, as discussed above, may include the O-arm® imaging system. The imaging system 24 may generate a plurality of two dimensional image data that may be used to reconstruct a three dimensional model of the subject 20 including one or more of the vertebrae 20v. The input image data may also be acquired at any appropriate time such as during a diagnostic or planning phase rather than in an operating theatre, as specifically illustrated in FIG. 1. Nevertheless, the image data may be acquired of the subject 20 with the imaging system 24 and may be input or accessed in block 104.

The image data acquired with the imaging system 24 may be of a selected image quality that may be difficult to identify various boundaries of image portions, such as the vertebrae 20v. Nevertheless, as discussed further herein, a neural network may be used to automatically identify the boundaries of the imaged portions to segment the image data.

The image data from block 104 may be processed with a selected system, such as a neural network or an artificial neural network, in block 106. The artificial neural network (ANN) may be a selected appropriate type of artificial neural network such as a convolutional neural network (CNN). The CNN may be taught or learn to analyze the input image data from block 104 to segment selected portions of the image data. For example, as discussed above, the CNN in block 106 may be used to identify boundaries of vertebral bodies in the image data from block 104. As discussed above the boundaries of the vertebral bodies may be displayed on the display device 32 either alone and/or in combination with the image 30. Accordingly, output segmented image data or output segmented data may be made in block 110. The outputted segmented data may be stored in a selected memory system, such as the navigation memory 74 or a segmented image memory 112 (See FIG. 1). The output segmented image data may segment selected portions, such as the vertebrae 20v as discussed above, for various purposes.

Accordingly, the flowchart 100 can start in block 102 and then access or input image data in block 104 to output segmented image data (and/or segmented masks) in block 110 and display or store the segmented image data in block 114. The process may then end in block 118 and/or allow for further processing or workflow, as discussed further herein. It is understood that the selected portions of the flowchart or process 100, however, may include a plurality of additional steps in addition to those discussed above. For example, the CNN may be developed and then taught to allow for an efficient and/or fast segmentation of a selected portion of the image data that is accessed or inputted from block 104. The segmentation may be a specific, such as identifying the vertebrae, or general such as identifying selected boundaries or changing contrast in the image data.

Figure 3:
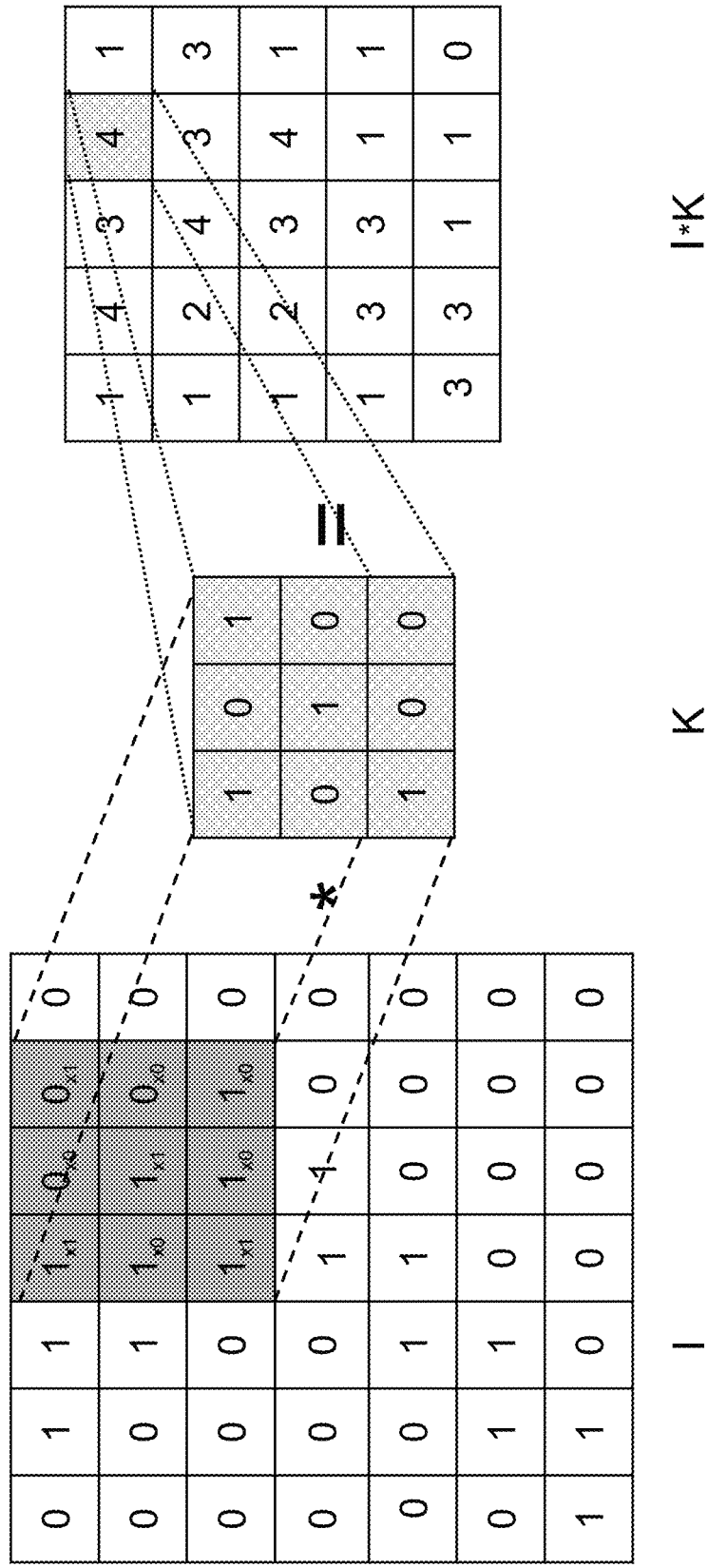

Turning reference to FIG. 3, the CNN used in block 106 may be developed and taught, as briefly discussed above, and discussed in further detail herein. The CNN is based upon generally known convolutional neural network techniques such as that disclosed in Özgün Çiçek, Ahmed Abdulkadir, Soeren S. Lienkamp, Thomas Brox, Olaf Ronneberger, "3D U-Net: Learning Dense Volumetric Segmentation from Sparse Annotation", International Conference on Medical Image Computing and Computer-Assisted Intervention, Springer, Cham, pp. 424-432 (2016) (https://arxiv.org/pdf/1606.06650.pdf (2016)), incorporated herein by reference. The CNN may be developed to efficiently identify selected portions of images by analyzing the image data and causing an excitation of an artificial neuron to make a judgment or calculation of a selected learned portion in a new input. According, the input image data from block 104 may be analyzed or processed with the CNN in block 106 based upon a teaching of the CNN, as discussed further herein.

With continued reference to FIG. 3, the CNN generally allows for the teaching of the CNN to identify image features in image data, such as the accessed image data in block 104. For example, a kernel K or filter of a selected dimension that may be previously defined and/or learned by the CNN. The kernel or filter K may then be applied to the image I in a stepwise manner, such as moving the filter one pixel or one voxel at a time. The filter K is a single component in the CNN which may consists of hundreds or thousands of interconnected filters arranged in layers. As discussed herein, the first layer filters operate on the image I, filters on the next layers operate on the output of the previous layers. That is, as illustrated in FIG. 3, the kernel K of a selected size may be moved stepwise a selected dimension, such as one pixel or voxel, throughout the entire image. The filter K may be learned and used to identify a selected portion or an "interesting" portion of the image. As illustrated in FIG. 3, the filter or kernel (K) is applied to an image (for example a two dimensional image). A product, or summation of products (such as a dot product of the kernel K and portion of the image I) may then be saved or stored for a further layer as a convolutional product matrix I*K. The product matrix, will have a dimensions less than the input given the size of the filter and the stride selected. The summation in a two dimensional manner is illustrated or defined by equation one (Eq.1):

$$(I*K)_{x,y} = \Sigma_{i=1}^{h} \Sigma_{j=1}^{w} K_{ij} \cdot I_{x+i-1, y+j-1} \quad \text{Eq.1}$$

Eq. 1 includes the image data I (i.e. includes pixels or voxels) in a selected array. The K represents the kernel or filter where the filter has a height and width (i.e. in a two dimensional kernel relating to two dimensional image data) and the output I*K of convolutional matrix is the summation dot product of the input image I and the kernel K according to Eq. 1.

Figure 4:
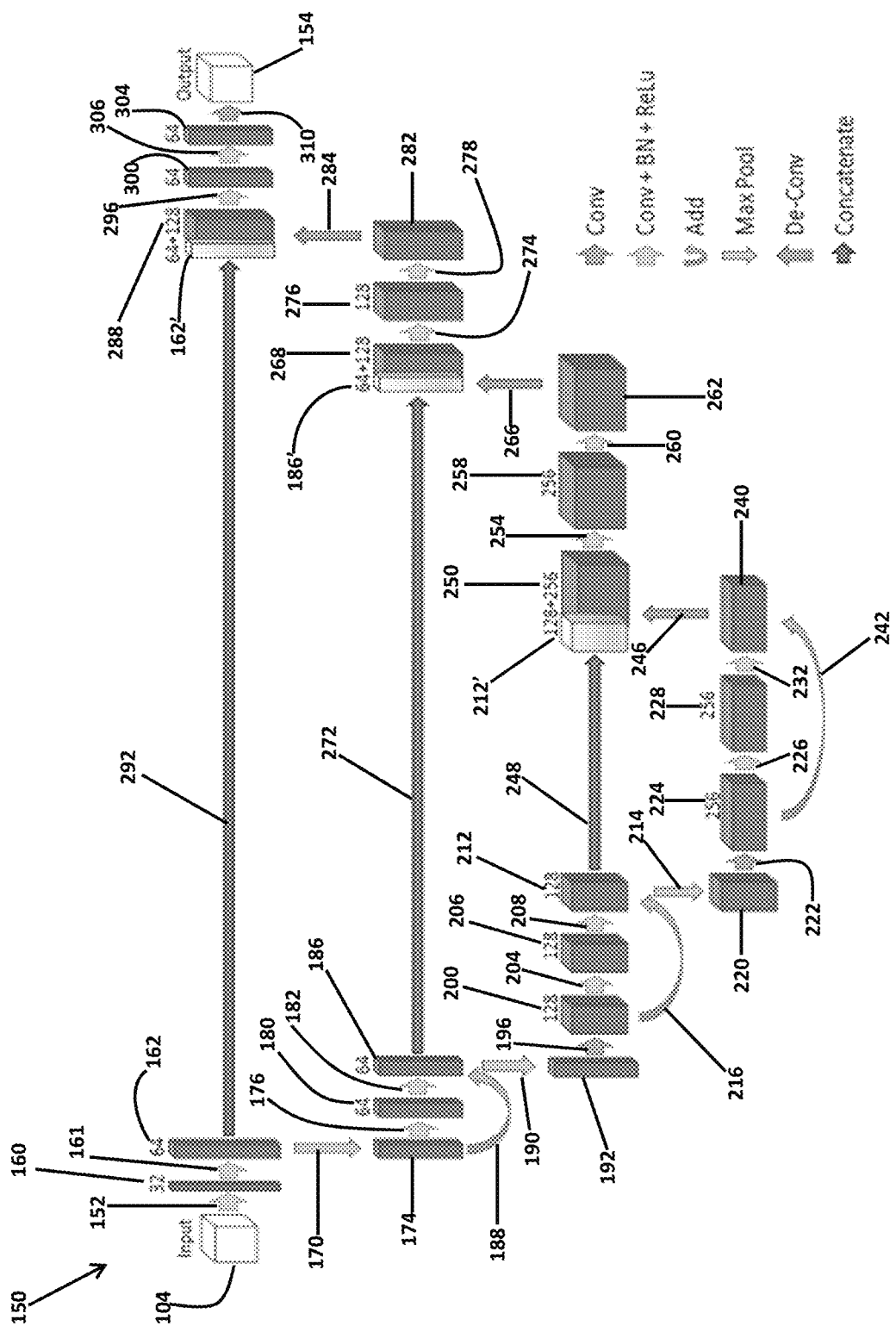

The convolution, as discussed further herein, includes moving the kernel over the input image to generate an activation map, of which the I*K is a part. As illustrated in FIGS. 3 and 4, an activation map layer is formed by the application of each filter to the image. A plurality of the filters, which may be learned by the CNN, may then be stacked to produce the output volume (e.g. for three dimensional image data) that generates a segmentation of the input image data. Thus, the CNN may output a three-dimensional (3D) output image or model that includes or is a segmentation of the image data.

Various features may be incorporated into the CNN, including those as known in the art and/or additional features to assist in determining and creating an efficient segmentation of a selected image. For example an amount of connectivity may include a local connectivity that is equivalent to the selected filter or kernel size. It is understood that kernel size may be selected based upon a resolution of an input image, a processing speed selected, or the like. In various embodiments the kernel size may be selected to be about 3×3×3 in size, such as pixel dimensions. It is understood, however, that different kernel sizes may be selected.

A size of an output may also be dependent upon various parameters that are selected to choose or select an output volume. For example, various parameters may include depth, stride, and a zero-padding or any appropriate padding. Depth includes a number of distinct different kernels that are convolved in a layer. For example, as illustrated in FIG. 3 the kernel includes a selected array of convolution operations (i.e. an array of ones and zeros). It is understood that a plurality of different filters may be applied to each layer in a CNN where the kernel includes different operational arrays. A stride refers to the number of elements (e.g. pixels, voxels, or other selected image element) that determine the amount of movement of the filter within the input volume per step. Padding may further be added to an input image in any particular layer to account for the decrease in an output image side due to the striding of a kernel within an image. As illustrated in FIG. 3, moving the kernel with a stride equal to one pixel will decrease the output matrix by two pixel dimension (e.g. an input of 7×7 having a kernel 3×3 with a stride of 1 will output a matrix of 5×5). Padding the input to include zero image data or pixels can maintain the output size to be equal to the input size of the volume or image.

In the CNN, in addition to the convolution including the size of the filter and features of the filter, as discussed above, additional operations may also occur. For example, in the CNN a pooling layer may be added to down sample the output. For example a pooling, such as a max-pooling, operation may attempt to reduce the number of parameters and reduce or control over fitting. The max pooling may identify or select only the maximum volume (e.g. a maximum pixel or voxel value) within a filter size for an output. For example, a max pooling filter may include a 2×2 filter that is applied in a stride of two along a selected dimension, such as two dimensional image for a two dimensional image. The max pooling will take only the maximum valued pixel from the filter area to the output.

Additional operations may also include batch normalization such as that described in Sergey Ioffe, Christian Szegedy, "Batch Normalization: Accelerating Deep Network Training by Reducing Internal Covariate Shift", ICML, 2015 (https://arxiv.org/abs/1502.03167 (2015)), incorporated herein by reference. The batch normalization may be applied at selected points or layers in the CNN, such as an initial layer or after each convolutional layer. The batch normalization may cause or will cause an activation throughout the CNN to achieve a selected distribution, such as a unit Gaussian distribution, at a selected point in the training, such as a beginning point in the training. Batch normalization allows increased depth of the network, accelerated training, and robustness to initialization.

An output from a neuron in a layer may include calculating a weighted sum and adding a bias to an activation function is then applied to the input and bias to produce an output. The weights from a neuron or layer output may be further analyzed or incorporated into the CNN. The output from neurons, to achieve the selected output, may have a weighted loss function to assist in activating or reducing an influence of a selected activation function of a neuron. A weighted loss function gives different importance to different labels based on certain properties, e.g. boundary of an object vs non-boundary An output from a neuron includes the activation function that is a rectified linear unit function except for an output layer function that is a soft max activation function. The activation function may include a function such as softmax function, or normalized exponential function as is generally known in the art. A rectified linear units function is a function generally defined as $f(x)=\max(0,x)$. Accordingly, the rectified linear units function can provide an activation of a neuron in the CNN when the rectified linear unit activation function is greater than a selected threshold. In the rectified function only a positive component of the function is compared to the threshold. In an output layer, the mask or delineation of a selected portion of the input image identified as a selected object (also referred to as a label, e.g. a vertebra or portion thereof) is determined if the output probability map is above a selected threshold probability, such as 35%. In various embodiments, the mask or delineation of the portion of the input image identified as a selected object is the label with the highest probability as opposed to a selected threshold or only a selected threshold.

The kernel in a three dimensional image may include a height, width, and depth. The kernel or filter may then be passed over the image to determine if a neuron is activated and generate an activation map based upon the presence or lack thereof of an activation, as described above. The filter or kernel K may then be determined or formulated to activate based upon a selected feature, such an edge or other identified portion. In the current system, a gold standard or learning image set may be used to teach the CNN the filter or kernel that identifies the selected or gold standard portion, such as the delineation, as discussed above, of a vertebrae. In moving the filter over the image data it is known to convolve or evaluate the image data based upon the filter or kernel K.

In addition to convolution layers and down sampling layers, a deconvolution layer(s) may be applied. The deconvolution layers are applied to upsample a final segmentation map at the resolution of the original image. In various embodiments, the deconvolution layers may densify a sparse activation. The deconvolution layer may also be referred to as a transposed convolution as described in A guide to convolution arithmetic for deep learning, V Dumoulin, F Visin—arXiv preprint arXiv:1603.07285, arxiv.org (2016), incorporated herein by reference.

In light of the above, and with reference to FIG. 3, a CNN network architecture is schematically illustrated in FIG. 3. The CNN schematic architecture 150 is exemplary illustrated to include an encoder part or portion that is to initially convolute and analyze the image according to the selected learned filters. The convoluted data may then be expanded or decoded using a subsequent deconvolution to produce the full resolution output 154. As discussed above, the image input 104 may be the input for generating the CNN and trained model (i.e. when inputting the gold standard or user identified boundaries), and/or relating to the image data that is attempted to segment it for identification of various portions in the image data, as discussed further herein. In FIG. 4, the schematic architecture illustrates a deep learning CNN including a plurality of layers.

With continuing reference to FIG. 4, the input data 104 may initially be involved or be analyzed by a convolution or one or more convolutions (e.g. two convolutions) of a filter of 3×3×3. After the convolution a batched normalization (as discussed above) may be applied, and a rectified linear unit. This may be initially applied in process 152 and generate a first analysis block 160 with 32 filters. A process 161 may include the same steps as process 152 and generate a second analysis block 164 with 64 filters. A max pooling step or process 170 is performed by applying a 2×2×2 max pooling with a stride of 2 to a first residual block 174. The first residual block 174 may then have the two convolutions, a batch normalization, and a rectified linear unit applied in a process 176 to generate a third analysis block 180. The third analysis block 180 may then again have the two 3×3×3 convolutions, followed by a batch normalization, and a rectified linear unit in process 182 to output a fourth analysis block 186. An addition process 188 of the first residual block 174 is added to the fourth analysis block 186. This may generate a second residual block 192.

A max pooling process or operation 190 is performed on the second residual block 192 and then in an additional layer it is convolved by two 3×3×3 convolutions in process step 196 to generate the fifth block 200. Again, a two 3×3×3 convolution, a batch normalization, and a rectified linear unit process 204 is performed on the fifth block 200 to generate a sixth block 204 followed again by two 3×3×3 convolutions, a batch normalization, and a rectified linear unit in process 208 to form a seventh block 212. To the seventh block 212 may be added the fifth block 200 in an addition process 216. To the seventh block 212 is applied a max pooling process 214 to output a third maxed pooled block 220.

The third max pooled block 220 may convolved with two 3×3×3 convolutions in process 222 to form an eighth block 224. The eighth block 224 may then have the two 3×3×3 convolution, batched normalization, and rectified linear unit process 226 to form a ninth block 228. The ninth block 228 may also have the two 3×3×3 convolution, batched normalization, and rectified linear unit applied in process 232 to form the tenth block 240. The eighth block 224 is added to the tenth block 240 as a residual in the addition process 242.

In a synthesis process, the tenth block 240 is deconvoluted in a deconvolution process 246 and the seventh block 212 is concatenated in process 248 to form a first synthesis block 250. The first synthesis block 250 may also then have two 3×3×3 convolutions, a batch normalization and a rectified linear layer process 254 applied thereto to generate the second synthesis block 258. Again a two 3×3×3 convolution, a batch normalization, and a rectified linear unit process 260 may be done to generate the third synthesis block 262 to which a deconvolution process 266 is applied to generate a fourth synthesis block 268 to which is added the fourth analysis block 186 in a concatenate process 272.

The combination of the fourth analysis block 186 and the fourth synthesis block 268 then has two convolutions of 3×3×3, a batch normalization, and rectified linear unit process 274 to generate the fifth synthesis block 276. Fifth synthesis block 276 has the two 3×3×3 convolutions, a batch normalization, and a rectified linear unit activation process 278 to generate the sixth synthesis block 282. The sixth synthesis block 282 is deconvoluted in a deconvolution process 284 to form a seventh synthesis block 288 to which is concatenated the second analysis block 162 with a concatenated process 292. The combination block is then further applied a two 3×3×3 convolution, batch normalization, and rectified linear unit process 296 to form the eighth synthesis block 300 and a ninth synthesis block 304 is generated after the process 306 of two 3×3×3 convolutions, batch normalization and rectified linear unit process.

Finally, a 1×1×1 convolution process 310 is applied to the ninth synthesis block. The convolution process 310 may include the soft max activation as discussed above. The process 310 generates the output 154 that may be the output segmented image data 110, as illustrated in FIG. 2. The output may include a selected number of channels, such as two channels that may be achieved due to the soft max activation in process 310. Further, the output 154 may include a 3D model or image that may be displayed for viewing by the user 12. Further, as illustrated in FIG. 4, the total number of filters applied in each operation is illustrated and may include a total for the CNN 150 may be 2,400. It is understood, however, that appropriate selected number of filters may be different than 2,400 and may include about 100 to about 20,000,000. Accordingly, 2,400 filters is disclosed herein as providing an efficient and faster CNN 150, such as for segmentation as discussed further herein.

The schematic architecture illustrated in FIG. 4 may then be applied for training and/or testing or segmenting selected images. In various embodiments, with reference to FIG. 5, a training phase process 350 is illustrated. The training phase process 350 may start with an input and may include an image data 352 that may be appropriate image data, such as the image data discussed above in block 104. Inputs may further include a segmentation mask, such as a binary segmentation mask 356. The segmentation mask 356 may be a standard or training data segmentation, such as a gold standard or user determined segmentation. For example, the binary segmentation mask may include a user (e.g. trained expert, such as a surgeon) segmentation of a selected structure, such as a vertebra including the vertebrae 20v.

After the input, including the image data 352 and the mask 356 selected steps may occur that included selected preprocessing. For example, an optional resizing step in block 360 may occur to resize the image data to an appropriate or selected size. In various embodiments, voxels may be resampled to a specific resolution, such as about 1.5 mm×1.5 mm×1.5 mm. Further preprocessing may include zero padding in block 364. As discussed above, zero padding may allow for insuring that an image size is achieved after or during the CNN process and also for insuring that selected augmentation maintains all image data within bounds of the image.

Selected augmentation may also be selectively applied to the image data in block 368. The augmentation in block 368 may be selected augmentation, such as augmentation of the input data, which may be both or only one of offline or online. Selected offline augmentation may include randomly scaling the images along a selected axis by a selected scale factor. Scale factors may include between about 0.9 and about 1.1 but may also include other appropriate scale factors. Further, images may be randomly rotated around selected axes at a selected amount. Again selected amounts of rotation may include such as about minus 10 degrees to about plus 10 degrees. Online augmentation may include randomly flipping images along different axes or transposing image channels. The augmentation in block 368 may assist in training the CNN by providing greater variability in the input image data 352 than provided by the image data set itself. As discussed above, and generally known in the art, the attempt is to have the CNN generate the filters that allow for automatic detection of selected features, such as segmenting boundaries of vertebrae, within the image data without additional input from a user. Therefore, the CNN may better learn or more effectively learn appropriate filters by including data that is more randomized or more highly randomized than provided by the initial image data.

The image data may then be normalized in block 272. In normalizing the image data, the variables are standardized to have a zero mean and a unit variance. This is performed by subtracting the mean and then dividing the variables by their standard deviations.

A cropping or patch wise process may occur in block 380. In various embodiments to achieve selected results, such as a decrease training time, reduce memory requirements, and/or finer grain detail learning, a selected cropping may occur. For example, an image data of a selected size may be cropped, such as in half, to reduce the amount of image trained at a time. A corresponding portion of the segmentation mask in block 356 is also cropped and provided in the image and mask in block 380. The cropped portions may then be combined to achieve the final output. The cropping process in block 380 may also reduce memory requirements for analyzing and/or training with a selected image data set.

The image data, whether cropped or not from process 380 may then be inputs to the CNN in block 384. The CNN in block 384, as discussed above, for example in FIG. 4, may then work to determine filters to achieve the output 154. The output 154 may include a probability map 388 and a trained model 390 as illustrated in FIG. 5. The probability map 388 is a probability of each voxel, or other selected image element, belonging to a selected labeled or delineated portion, e.g. a vertebra, a portion of a vertebra, a screw, or other selected portion in the input image. It is understood by one skilled in the art that the input image may include various selectable portions, such as a vertebra, a plurality of vertebrae, a screw, etc. A threshold probability may be selected, in various embodiments, for identifying or determining that a selected image portion is a selected portion or label. It is understood, however, that a threshold is not required and that probability map may output selected probabilities in the output for the segmentation.

The trained model 390 includes the defined filters that may be applied as the kernels K discussed above and may be based on the probability map 388. The defined filters, as also discussed above, are used in the various layers to identify the important or significant portions of the image to allow for various purposes, such as segmentation of the image. Accordingly, the trained model 390 may be trained based upon the input image 352 and the binary segmentation mask 356. The trained model may then be stored or saved, such as in a memory system including the navigation memory 72, for further access or implementation such as on the image memory 112 and/or the navigation memory 74. The training process 350 may include various inputs, such as an amount of padding or a selected voxel size, but is generally performed by a processor system executing selected instructions, such as the navigation processor system 70. For example, the training of the CNN in block 384 and the training model 384 may be substantially executed by the processor system.

It is understood, however, that the trained model may also be provided on a separate memory and/or processing system to be accessed and used at a selected time. For example, the trained model may be used during a planning phase of a procedure, and/or, during a procedure when the subject 20 is in an operating theater during an implantation procedure.

With additional reference to FIG. 5 and turning reference to FIG. 6, the trained model 390 from the training phase 350 may be used as an input when attempting to determine a segmentation of an image, such as an image of the subject 20, in a segmentation phase 400. Accordingly, according to various embodiments, the image data of the subject 402 may be input with the trained model 390. As discussed above inputting the image data 402 and the trained model 390 may include accessing both the image data and the trained model that are stored in a selected memory, such as those discussed above, by one or more of the processor systems including the navigation processor system 70.

The image data 402 may be preprocessed in a manner similar to the image data preprocessed during the training phase 350. For example, the image data 402 is preprocessed in the same manner as the trained model 390 is trained. As discussed above, various preprocessing steps are optional and may be performed on the image data 350 during the training phase. During the segmentation phase 400 the image data 402 may be or is selectively preprocessed in a similar manner. Accordingly, the image data 402 may be resized in block 360', zero padding may be added in block 364', the image data may be normalized in block 372'. It is understood that the various preprocessing steps may be selected and may be chosen during the segmentation phase 400 if performed during the training phase 350. The segmentation image data is the same type as the training image data.

After appropriate preprocessing is performed in blocks 360', 364', and 372', the image data 402 may be split or cropped, in block 410. The splitting of the image in block 410 is also optional and may be selected based upon processing time, memory availability, or other appropriate features. Nevertheless, the image 402 may be split in a selected manner, such as along selected axes. The image data may then be merged, such as in a post processing step 414 once the segmentation has occurred.

Once the image data is preprocessed, as selected, the CNN 384, with the learned weights and/or filters may be used to segment the image data 402. The segmentation of the image data 402 by the CNN 384 may create an output 420 including a probability map 416 and a selected mask, such as a binary segmentation mask in the output 422. The output 420 may be an identification of a selected geometry of the segmented portions, such as the vertebrae 20v or other selected features. The CNN 384, having been taught or learned the selected features and weights, may segment the portions of the image data, such as the vertebrae.

In the output 420, probability map 416 is a probability of each voxel, or other image element or portion belonging to a selected label or portion, such as a spine, vertebra, vertebrae, screw, etc. The binary segmentation 422 is produced from the probability map 416 by selecting all the voxels or other image portions with a probability greater than a threshold. The threshold may be any selected amount, such as about 30% to about 99%, including about 35%. It is further understood, however, that a threshold may not be required for performing the binary segmentation 422 based on the probability map 416.

The segmentation process 400 may include various inputs, such as an amount of padding or a selected voxel size, but is generally performed by a processor system executing selected instructions, such as the navigation processor system 70. For example, the segmentation with the CNN in block 384 and the output segmentation in block 420 may be substantially executed by the processor system. Thus, the segmentation process 400, or substantial portions thereof, may be performed substantially automatically with the processor system executing selected instructions.

The output 420 may then be stored in a selected memory, such as the imaging memory 112 and/or the navigation memory 74. In various embodiments, the segmentation output 420 may be saved in the navigation memory 74 for use in various workflows, as discussed further herein. Moreover, the output may be output as a graphical representation, such as one or more icons representing the geometry of the segmented vertebrae. As illustrated in FIG. 1, the segmented portions may be displayed either alone or superimposed on the image 30 such as vertebrae icons or masks 20vi' and 20vii'. It is understood that any appropriate number of segmentations may occur, and the illustration of two vertebrae in FIG. 1 is merely exemplary. For example, the image data 402 may be of an entire spine or all vertebrae of the subject 20. Accordingly, the segmentation mask may include an identification of each of the vertebrae. Moreover, it is understood that the segmentation may be a three dimensional segmentation such that an entire three dimensional geometry and configuration of the vertebrae may be determined in the output 420 and used for various purposes, such as illustration on the display 32.

The navigation system 10, as illustrated in FIG. 1, may be used for various purposes such as performing a procedure on the subject 20. In various embodiments, the procedure may include positioning an implant in the subject, such as fixing a pedicle screw within the subject 20, such as into one or more of the vertebrae 20v. In performing the procedure, the tool 16 may be an implant, such as a screw. It is understood that various preliminary steps may be required for performing or placing the implant, such as passing a cannula through soft tissue of the subject 20, drilling a hole into the vertebrae 20v, tapping a hole in the vertebrae 20v, or other appropriate procedures. It is further understood that any of the items used to perform various portions of the procedure may be the tool 16 and that the tool 16 may also be the implant. Any one of the portions (e.g. implants or tools or instruments) may be tracked with the respected tracking system, such as simultaneously or in sequence, and navigated with the navigation system 10. During navigation, the navigation system 10 may display a position of the tool 16 as the icon 16i on the display 32. In a similar manner, other instruments may be navigated simultaneously with the instrument 16 such that the instrument 16 may include a plurality of instruments and all or one may be individually or multiply displayed on the display device 32, according to instructions such as those from the user 12.

Figure 7B:
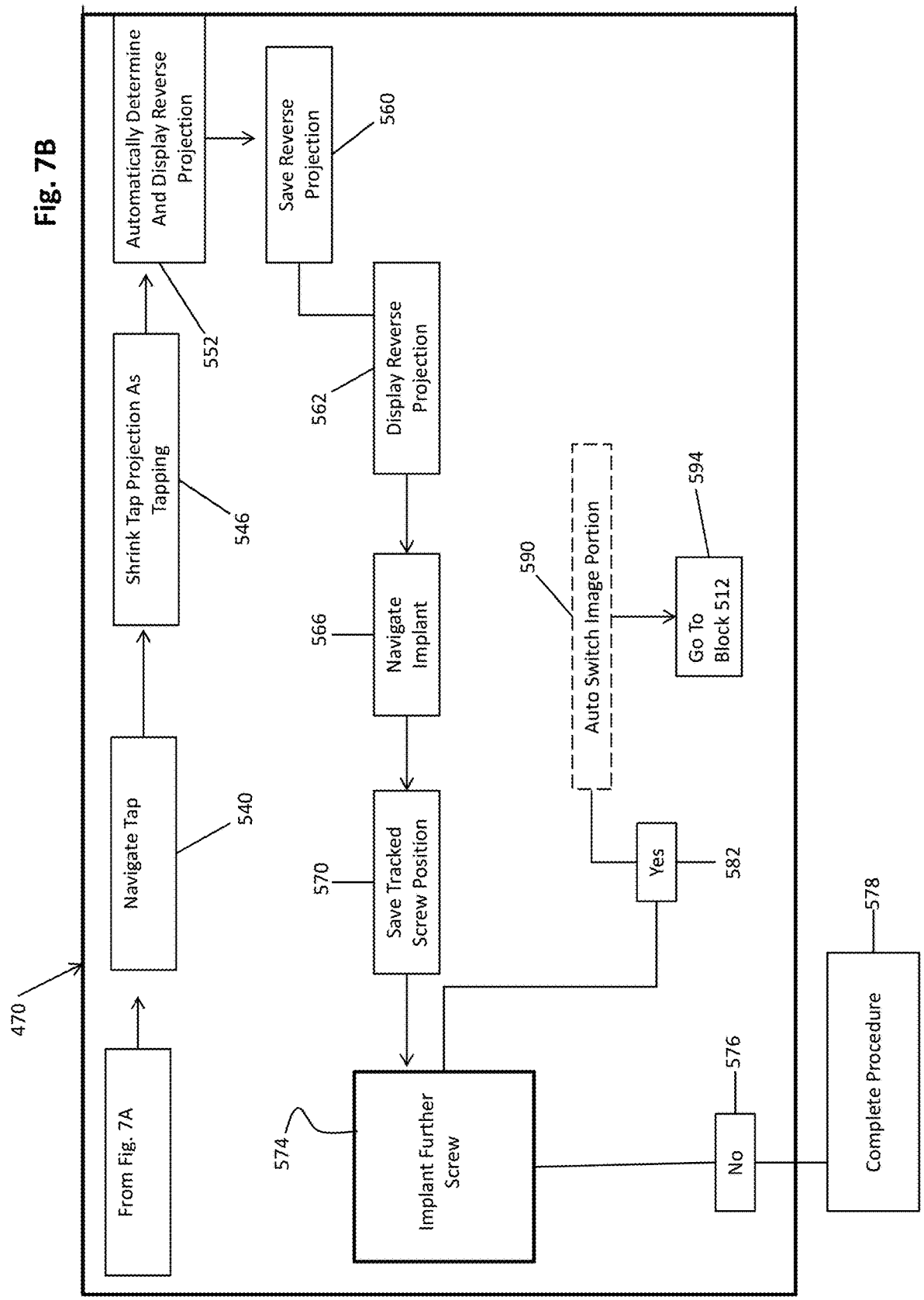

The navigation system 10, therefore, may be used to perform the procedure on the subject 20 by the user 12. Further, the navigation system 10 including the navigation processing unit 70 may execute instructions that are stored on selected memories, such as the navigation memory 74, for performing or assisting the user 12 in performing a procedure on the subject 20. According to various embodiments, such as those illustrated in FIG. 7A and FIG. 7B. As illustrated in FIGS. 7A and 7B a workflow diagram 450 includes various features and steps that may be performed by a user, or at the direction of the user 12, and/or substantially automatically by executing instructions by the processor system, including the navigation processor system 70, based upon the instruction of the user 12 or in light of a previous step.

The workflow 450 may include a data acquisition or accessing step or portion including operating the imaging system 24, such as an O-arm® imaging system, in block 456 to acquire an image scan or image data of the subject in block 460. The image data may then be accessed or received via a connection or communication 462. As discussed above, in relation to FIG. 2, the image data may be accessed in block 104. Accessing or inputting data, such as the image data, in block 104 may be similar or equivalent to the processor accessing the data 462. Similarly, as discussed further herein, the image data may be analyzed and segmented such as with the automatic segmentation process 400 illustrated in FIG. 6. Regardless, the image data 460 may be acquired or accessed by the navigation processor system 70 to allow for a workflow, including the workflow 450 to occur. The workflow 450 may further include an automated or semi-automated workflow portion 470 that includes analyzing the image data 460 and/or performing the portions of the procedure.

As discussed above the process 462 allows the image data from block 460 to be used by the navigation processor system 70 according to the selected navigation process system 470. The surgical navigation system 470 may include portions that are either entirely automatic (e.g. performed by a processor executing instructions according to a predetermined algorithm, a processor system executing a deep learning or neural network system, etc.) or portions that are a combination of manual input and automatic determination. As discussed further herein, various elements or portions may be substantially automatic unless identified as including a manual portion. It is understood, however, that manual portions may be not included as discussed further herein.

In the surgical navigation process 470, the navigation system 10 may be initiated or started in block 474. The starting of the navigation system in block 474 may be substantially manual, such as by the user 12, turning on or starting the navigation system 10. It is understood, however, that the navigation system 10 may also initiate substantially automatically such as when entering a selected location, such as an operating theater. After initiating or starting of the navigation system in block 474, a selection of a surgeon in block 476 may be made and a selection or a procedure in block 478 may be made. It is understood that selecting the surgeon in block 476 may be optional. Nevertheless, the navigation memory 74 may have selected saved surgeon preferences and/or operation that may be specific to an individual surgeon, such as the user 12. Therefore, selecting the surgeon in block 476 may cause the navigation processing unit 70 to access the memory 74 to select or determine preferences for the user 12 based upon the selection of the surgeon in block 476. The specific surgeon may have preferences that may augment one or more of the following items such as specific instruments to be prepared for a selected procedure, a size of an implant for a selected anatomical structure, or the like. In various embodiments for example, a selected surgeon may select to include an implant, such as a pedicle screw, that has a 3 mm clearance relative to a boundary of the vertebrae while another surgeon may select to include a pedicle screw that has a 5 mm clearance. Accordingly, the selected surgeon having the identified preferences may be used by the processor system in executing the processes 470 to select and/or identify selected instruments during navigation.

A selection of the surgeon in block 476 and the selection of the procedure in block 478 may be substantially manually input, such as using the input 72 or any appropriate manual input 72 to the navigation processing unit 70. It is understood that the user 12 may manually input both the selection of the surgeon in block 476 and the selection of the procedure in block 478 or may direct that the selections in blocks 476 and 478 be made. Nevertheless, it is understood that the selection of the surgeon in block 476 and the selection of the procedure in block 478 may be substantially manual.

The navigation process 470 may automatically suggest an instrument set based upon either one or both of the selected procedure in block 478 or the selected surgeon in block 476. Automatically suggesting an instrument set in block 482 may include selecting or suggesting instrument tools, implants, or the like. For example, with regard to the placement of a pedicle screw the navigation process 470 may suggest an instrument (e.g. a probe, an awl, a driver, a drill tip, and a tap) and/or implant type and or geometry and size (e.g. a screw size and length). The suggestion of an instrument and/or implant set in block 482 may be based upon a selected algorithm that accesses a database of possible procedures and identifies tools therefrom. Further, a machine learning system may be used to identify an instrument set based upon various inputs such as the procedure and surgeon, as selected surgeons may select different instruments and/or a surgeon's preference (e.g. pedicle screw size) may vary or change a selected instrument set. Instrument selection may also be made or assisted with heuristics based on the segmentation as one of the inputs. Whether the instrument set is automatically suggested in block 482 or not, instruments may be verified in block 484. The verification of the instruments may be insuring that the instruments are present in an operating theater and/or inputting them to the navigation system 10. For example, the navigation system 10 may be instructed or used to identify a selected set of instruments or type of instrument.

The instruments in a navigated procedure are generally tracked using a selected tracking system. It is understood that appropriate tracking systems may be used, such as an optical or an EM tracking system as discussed above. In various embodiments, therefore, an instrument tracker may be identified in block 486. An identification of the instrument tracker may be substantially automatic based upon the tracker being identified by the selected tracking system, such as with the optical localizer 82. For example, the optical localizer may be used to identify or "view" the tracking device, such as the instrument tracking device 56. It is understood that a plurality of instruments may have a plurality of unique trackers on each of the instruments and therefore a viewing of a selected tracker may be used to identify the tracker to the instrument. It is understood, however that trackers may be changeable and therefore an automatic detection may not be possible and therefore a manual identification of the instrument tracker may be selected.

A tip associated with a selected instrument may be automatically identified in block 490. As discussed above, the automatic identification of the tip may be used by "viewing" the tip with the optical localizer 82. Accordingly, the navigation processor 70 may use a deep learning system, such as a CNN, to identify the tip relative to the instrument and/or the tracker identified at block 486. By identifying the tip, the process of the procedure and the user may be assisted in identifying selected features. Features may include a geometry of the tip used during navigation and displaying on the display device 32, such as with the instrument icon 16i. It is understood, however, that the tip may also be manually inputted or identified in selected procedures.

In a navigated procedure the patient 20 may also be tracked with the DRF 60. In block 496 the DRF 60 may be placed or identified on the patient 20. It is understood that placing the DRF 60 on a patient is generally a substantially manual procedure being performed by the user 12 or at the instruction of the user 12. Nevertheless, the placement of the DRF 60 may also include identifying or tracking of the DRF 60 in the navigation process 470. Accordingly, the navigation process 470 may include tracking the DRF once placed on the patient 20. The DRF allows for registration in block 498 to the image data input via the process 464 from the image data 460. Registration can be according to any appropriate registration process including those generally known in the art, as discussed above.

Registration allows for a subject or physical space defined by the subject 20 to be registered to the image data such that all points in the image data are related to a physical location. Therefore, a tracked location of the instrument may be displayed on the display device 32 relative to the image 30. Further the registration may allow for image portions to be registered to the patient, such as segmented portions.

Segmented portions may be segmented in block 502 (e.g. vertebrae) and segmentations may be displayed on the display device in block 504. As discussed above, segmentation of selected image portions, such as vertebrae, may be performed substantially automatically according to selected systems, such as the CNN 150, as discussed above. In addition to or alternative to the segmentation as discussed above, the segmentation of image portions may, however, also be manual such as by the user 12 physically tracing with a selected instrument, such as the tracked probe on the display device, on the image 30. Nevertheless, the auto-segmentation in the navigation process 470 (e.g. with the segmentation process 400) may allow for the user 12 to not use surgical time or planning time to segment the vertebrae and allow for a faster and more efficient procedure. A faster and more efficient procedure is achieved by saving the surgeon time in manual interaction with the navigation system 10 including various software features thereof, e.g. by automatic selection of the correct tool projection based on the segmentation.

The segmentations may also be displayed, such as display segmentations in block 504, including the display of segmented icons 20vi' and 20vii'. The segmentation icons may be viewed by the user 12 and verified that they overlay selected vertebrae. In addition to or as a part of a verification, the image portions may also be identified and/or labeled in block 508. The labeling of the image portions may be manual, such as the user 12 selecting and labeling each vertebra in the image 30, including the segmented portions therein. The labeling and/or identification of the vertebrae may also be semi-automatic such as the user 12 identifying one or less than all of the vertebrae in the image 30 and the navigation processor 70 labeling all of the other vertebrae relative thereto. Finally, the identification of the vertebrae and labeling thereof in block 508 may be substantially automatic wherein the navigation processor 70 executes instructions, such as based upon the CNN 150, to identify selected and/or all of the vertebrae in the image 30 and display labels therefore relative to the segmented portions, such as the segmentation icons 20vi' and 20vii'.

The navigation process system 470, either during a procedure or during a planning phase, may also automatically select an implant parameter, such as a size (e.g. length and width), in block 512. As discussed above, the vertebrae may be segmented according to selected procedures in block 502. Upon segmenting the vertebrae, the dimensions of the vertebrae may be known, including a three dimensional geometry, including size and shape. This may assist in selecting a size of an implant based upon a segmented size or determined size of the vertebrae. Also, based upon the selected surgeon preferences, based upon a selected surgeon in block 476, a size of a vertebra relative to an implant may also be known and therefore will also assist in automatically selecting the implant parameters to a specific size. The size may be output, such as on the display 32 for selection and/or confirmation by the user 12. Accordingly, selecting the implant parameters, including size or other geometry, may be made by the process system 470.

The procedure 470 may then proceed to assist in preparing and/or placing a selected implant. To place an implant, such as a pedicle screw, an entry point into the patient 20 may be determined relative to the vertebrae 20v. With continuing reference to FIGS. 7A and 7B and additional reference to FIG. 8 the instrument 16 may include a probe 16p with the tracker 56 (e.g. an optical tracker). The probe 16p may be moved relative to the subject 20, such as without piercing the subject 20.

Figure 8:
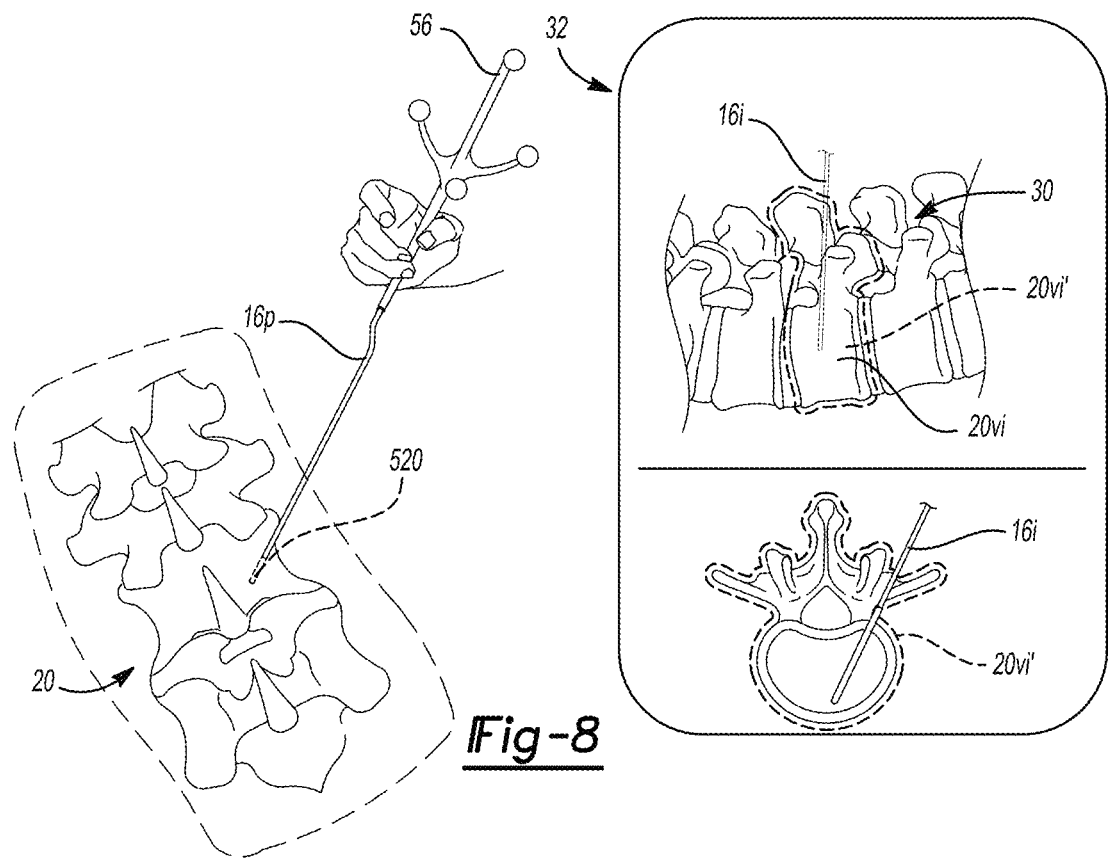
FIG. 8 is an environmental and display view of tracking and displaying an instrument projection.

In attempting to determine an entry point in block 516 the probe 16p may be moved relative to the vertebrae 20v. The vertebrae 20v, having been identified and/or labeled in block 508, may be identified based upon a projection from the probe 56, such as from a tracked distal end 520 of the probe. The probe end 520 need not puncture a soft tissue, such as a skin, of the subject 20 but rather the projection may be determined and/or displayed, such as with the instrument icon 16i on the display device 32, as illustrated in FIG. 8. The instrument icon 16i may change based upon the selected instrument and may be displayed as a projection of the probe or just a trajectory based upon the position of the probe 16p relative to the vertebrae 20v. Based upon the projection of the probe the vertebrae may be identified, such as the vertebrae 20vi in the image 30 on the display device 32. The display device 32 may display the image 30 in various manners, such as in a medial and axial view.

The projection of the instrument 16i may be based upon a boundary of the vertebrae 20v, such as based upon the segmentation of the vertebrae in block 502. The segmentation may be manual, semi-manual, or substantially automatic (e.g. with the segmentation process 400). Nevertheless the projection icon 16i may be limited to a boundary of the vertebrae 20v and may be displayed either alone or in combination with the vertebrae icon 20vi'. It is further understood that the projection 16i may be based upon a geometry of selected tools such as a drill so that the user 12 may view the physical extent of the drill relative to the image 30 and the segmented vertebrae 20vi' to ensure that the drill would drill far enough into the vertebrae.

The navigation process 470, as discussed above, may include portions that occur substantially with the navigation processor 70 either alone or in combination with actions taken by the user 12. In various embodiments, the find entry point features may be used to then identify or mark a point on the skin of the subject 20. It is understood that marking the incision point is not required. However, performing an incision to allow other instruments to enter the subject 20 may occur after finding the entry point as discussed above. Once an incision is made, a tool may be navigated, such as by tracking the tool and illustrating the position of the tool on the display device 32 in block 526. For example, after forming the initial incision, navigating an awl to the vertebrae identified in block 516 may occur. The tool may also be referenced to as an instrument.

In navigating the awl relative to the vertebrae, the awl may be passed through the incision in the skin and contact the vertebrae. An icon representing the awl or a projection from the tracked location of the awl may be illustrated relative to a vertebra at a selected time, such as when the awl is within a selected distance to the vertebrae (e.g. less than about 1 mm to about 6 mm, including about 5 mm). Thus, the icon representing the tool may auto display a selected implant size, such as an icon superimposed on the image 30 on the display device 32 in block 528.

Automatically display an implant size, or tool size or position, may include determining the size of an implant based upon the boundaries of the segmented vertebrae in block 502. The navigation process 470 may execute instructions that based upon the segmented image geometry (e.g. including size and shape) an implant may be automatically selected and displayed on the display device. When the awl is at a selected position relative to the vertebrae displaying the automatically selected implant may allow the user 12 to view a selected opportunity or selected implant. By automatically selecting the implant the user 12 need not separately measure the vertebrae and/or trial various implants relative to the vertebrae. Nevertheless, the user 12 may confirm and/or change the implant size in block 532. If selected, a different size implant may then be displayed relative to the vertebrae image 20vi and/or the segmentation 20vi'. The user 12 may then view the automatically displayed implant size in block 528 and/or a changed or confirmed size in block 532.

Further the user 12 may move the tracked awl relative to the vertebrae 20v to select a position of the implant relative to the vertebrae 20v. For example, a different position of the awl relative to the vertebrae 20v may cause the system 470 to determine or calculate a different size implant (i.e. the anterior boundary of the vertebrae is further away). Once the user 12 has selected an appropriate or selected trajectory, the trajectory may be saved. The trajectory may be saved by the user 12, such as using the input device 72. It is understood that the input device, however, may be appropriate devices such as a verbal command for audio input, a gesture, a footswitch, or the like. In addition the user's selection may be saved based upon the selected surgeon in block 476 for further or future reference.

The projection may be saved for future use and displayed and/or hidden as selected to allow for guiding of the tapping of the vertebrae 20v. With continuing reference to FIG. 7 and additional reference to FIGS. 9A, 9B, and 9C, the vertebrae 20v may be tapped with a tap while viewing the display device 32 when the tap is navigated. The tap may be navigated as it is moved relative to the vertebrae 20v by the user 12. The tap may be displayed as the icon 16i on the display device 32 relative to the image 30. Further, at a selected time, such as when the tap is near or in contact with the vertebrae 20v a projection of a tapped geometry 542 may be displayed relative to the image 30 including the vertebrae 20vi as navigating the tap in block 540 to the vertebrae 20v and displaying at the projection 542 of the tapped area or volume may allow the user 12 to confirm that the selected tapped volume based upon a projection of the tap into the vertebrae matches the implant projection or saved implant projection from block 536.

Once it is confirmed that the tap projection 542 matches the saved implant projection from 536 the tap may be driven into the vertebrae 20v, as illustrated in FIG. 9B. A reduced or shrunken tap projection 544 in block 546 may allow the user 12 to view the extent of the tapping relative to the projected or selected tap length volume. The shrunken tap geometry 544 in block 546 may allow the user 12 (FIG. 9B) to understand the extent of the tapping performed so far and the auto tapping remaining. Accordingly, the user may slow down driving of the tap into the vertebrae at a selected period while allowing for a fast and efficient tapping at an initial period.

It is understood that the processing system 70 may shrink the tapped projection, such as the shrunken tap projection 544 in block 546, substantially automatically based upon navigation of the tap relative to the vertebrae 20v. The tap projection is initially based upon the selected implant projection from block 536 based upon the implant, such as the automatically selected implant in block 528. Therefore, the navigation process 470 may allow for efficient tapping of the vertebrae 20v by allowing the user 12 to view the tapping in process and confirm when the tapping is completed.

When tapping is completed, a reverse projection 550 may be automatically determined and displayed in block 552. The reverse projection 550 may be substantially equivalent or equal to the tapped depth into the vertebrae 20v and based upon the amount of tapping or depth of tapping by the user 12. Further, the reverse projection of 550 may be substantially equivalent to the initial tapped projection 542, as illustrated in FIG. 9A. The reverse tap projection 550 may be maintained for viewing by the user 12 on the display device 32 relative to the vertebrae 20vi for positioning of the implant into the vertebrae 20v. Moreover the instrument icon 16i may be a combination of both the instrument portion and a now fixed or permanent tapped projection 542'. The fixed projection of 542' may be initially equivalent to the reverse projection 550 and allow the user 12 to view both the tapped volume (e.g. width and/or depth) relative to the instrument 16i and the vertebrae image 20vi.

The reverse projection may be saved in block 560 for various purposes, as discussed above for guiding or navigating the implant. Further the saved reverse projection may be equivalent to the tapped position and may also be saved under the selected surgeon 76 for further reference and/or future reference.

Figure 10:
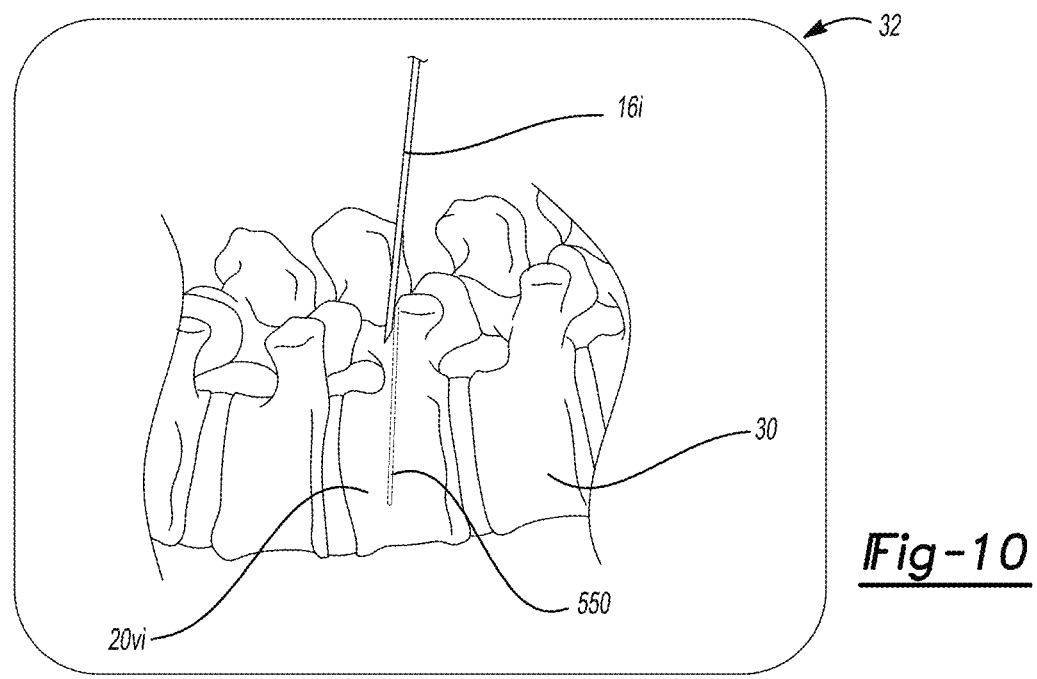
FIG. 10 is a display view of a reverse projection as a plan and a tracked view of an implant.

Once the tapping of the vertebrae is performed, the implant may be placed in the vertebrae 20v. With continuing reference to FIGS. 7A and 7B and additional reference to FIG. 10, the implant may include a screw, such as a pedicle screw, that is positioned within the vertebrae. The screw and a driver may be illustrated as the icon 16i on the display device 32 relative to the image 30 and the vertebrae 20vi. The reverse projection 550 may also be displayed in block 562 to assist in navigating the implant in block 566. As illustrated in FIG. 10, the implant may be illustrated as at least a part of the icon 16i such that the icon 16i may be aligned with the reverse projection 550 to allow for driving or placing the screw into the vertebrae 20v along the tapped trajectory and volume as illustrated by the reverse projection 550. Accordingly, navigating the implant in block 566 may allow the user 12 to position the implant in the selected and tapped location in the vertebrae 20v.

Tracking of the screw into the vertebrae 20v may also allow for a saved tracked position of the screw in block 570 for the selected surgeon from block 476 for future use. Accordingly various features, such as positioning of the tapped location and final position of the screw along with various other features, such as geometry and size of the screw may be saved for reference of a selected surgeon for future use.

After positioning the screw by navigating the implant in block 566 and/or saving the tracked screw position in block 570 a determination of whether further screws need be placed may be made in block 574. If no additional implants are to be placed a NO path 576 may be followed to complete the procedure in block 578. Completing the procedure may include decompressing vertebra, removing instrumentation from the subject 20, closing the incision, or other appropriate features.

If it is determined that a further screw is to be implanted in block 574 a YES path 582 may be followed. It is understood that the determination of whether an additional screw is to be placed may be based upon the selected procedure from block 478 or based upon a user input from the user 12. Accordingly, determining whether a further implant is to be positioned in block 574 may be substantially automatic or manual.

Regardless of the procedure for determining whether a further implant is needed, if the YES path 582 is followed an auto-switching to a further image portion in block 590 may optionally occur. For example, if a first screw is placed in an L5 vertebra a second screw may be placed in a second side of the L5 vertebra. Automatically switching to a separate image or view portion of the vertebrae may assist the user 12. Further, if a second implant is positioned in the L5 vertebra and the selected procedure is to fuse an L5 and L4 vertebra, the image 30 may automatically switch to display or more closely display the L4 vertebra for further procedure steps. Accordingly, auto-switching to another image portion in block 590 may assist the user 12 in efficiently performing the procedure.

Whether an optional automatic switching to additional image step is performed or not, the determination that further implants are to be placed may allow the navigation process 470 to loop to block 512 to automatically select parameters of the next implant and continue the procedure from there. It is understood that various other portions may also be repeated, such as identifying instruments or tips (e.g. blocks 486 and 490), but such application may not be required, particularly if the instrumentation maintains or remains the same from a first implant to additional implants. Nevertheless, a selected number of implants may be positioned in the subject 12 by continuing the process from block 512 to the decision block 574 until no further implants are determined to be necessary or part of the procedure and the no path 576 may be followed.

Accordingly, in light of the above, the navigation process 470 may be used to place implants in the subject 20, such as spinal implants, in a selected and efficient manner by allowing the processor system to assist the user 12 in performing various procedures and/or selecting various portions of the procedure, such as implant geometry and/or positioning, automatically. The user 12 may then use the selections as an initial starting point or confirm that the suggestions are appropriate and continue with the procedure. Accordingly a cold or "blank slate" is not required to perform the procedure by the user 12.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical navigation system configured for operation in a procedure, comprising:
   a memory system having stored thereon a neural network that is trained for analyzing an image data including to segment at least one member in an image data,
   a processor system configured to:
     receive an input from a user regarding at least a user identity;
     access the image data;
     access the memory system to execute the neural network to segment the image data;
     output a three-dimensional (3D) image data of the segmentation;
     output a workflow procedure, automatically, for at least a portion for a surgical procedure to be performed on the subject based on the output 3D image data and the received user identity;
   wherein the neural network includes at least one of a limited number of parameters or selected weights on parameters to increase a probability of correct segmentation.

2. The system of claim 1, wherein the image data is acquired with a cone-beam x-ray imager;
   wherein the neural network is a deep neural network.

3. The system of claim 1 wherein the segmentation delineates at least one member of the subject in the image data relevant to the surgical procedure.

4. The system of claim 3, wherein the segmentation delineates all of the members in the image data relevant to the surgical procedure.

5. The system of claim 1, further comprising:
   a display device to display;
   wherein the processor is configured to display the output 3D image data segmentation.

6. The system of claim 1, wherein the processor is further configured to execute instructions to:
   determine a dimension of the member in the output 3D image data segmentation;
   calculate at least one characteristic of an appropriate tool for the surgical procedure, wherein the characteristic includes at least a physical dimension of the appropriate tool.

7. The system of claim 6, wherein the appropriate tool includes at least one of an implant or an instrument to position the implant.

8. The system of claim 1, wherein the processor system is further configured to automatically output the workflow procedure includes automatically suggesting an instrument set for the workflow procedure.

9. The system of claim 8, wherein automatically suggesting the instrument set for the workflow procedure is based on the received user identity.

10. The system of claim 8, wherein automatically suggesting the instrument set for the workflow procedure is based on a determined procedure for the subject.

11. The system of claim 8, wherein the processor system is further configured to automatically output a tool icon displayed on the screen that includes a projection from a tracked distal tip of a tool to a portion of the image;
    wherein the projection is automatically determined and displayed based on the output 3D image data segmentation from the tracked distal tip of the tool.

12. The system of claim 1, wherein the processor is further configured to automatically determine at least a second vertebrae for placement of a second implant after completing placement of a first implant in a first vertebrae;
    wherein the processor is further configured to generate a display of the second implant and the second vertebrae.

13. The system of claim 1, wherein the processor system is configured to further automatically output to the user a determined at least one of a screw size and display the determined screw size icon relating the automatically determined screw size.

14. A method for navigating a procedure, comprising:
    providing on a memory system a neural network that is trained for analyzing an image data including to segment at least one member in an image data,
    operating a processor system to:
      receive an input from a user regarding at least a user identity;
      access the image data;
      access the memory system to execute the neural network to segment the image data;
      output a three-dimensional (3D) image data of the segmentation;
      output a workflow procedure, automatically, for at least a portion for a surgical procedure to be performed on the subject based on the output 3D image data and the received user identity;
    wherein the neural network includes at least one of a limited number of parameters or selected weights on parameters to increase a probability of correct segmentation.

15. The method of claim 14, further comprising:
providing the image data as acquired with a cone-beam x-ray imager;
providing the neural network as a deep learning neural network.

16. The method of claim 14, further comprising:
segmenting the image data to generate the segmentation that delineates at least one member of the subject in the image data relevant to the surgical procedure.

17. The method of claim 1, further comprising:
a display device to display;
wherein the processor is configured to display the output 3D image data segmentation.

18. The method of claim 14, further comprising:
displaying the output 3D image data segmentation;
further operating the processor to:
   determine a dimension of the member in the output 3D image data segmentation; and
   calculate at least one characteristic of an appropriate tool for the surgical procedure, wherein the characteristic includes at least a physical dimension of the appropriate tool.

19. The method of claim 14, further operating the processor to automatically suggest an instrument set for the workflow procedure based on one of the received of the user identity or a determined procedure for the subject.

20. The method of claim 14, further operating the processor to:
automatically determine at least a second vertebrae for placement of a second implant after completing placement of a first implant in a first vertebrae;
generate a display of the second implant and the second vertebrae;
wherein determining the second implant includes determining at least one parameter of the second implant relative to the second vertebrae.

* * * * *